US009517042B2

(12) United States Patent
Hsieh et al.

(10) Patent No.: US 9,517,042 B2
(45) Date of Patent: Dec. 13, 2016

(54) SYSTEMS AND METHODS FOR IMAGING PHASE SELECTION FOR COMPUTED TOMOGRAPHY IMAGING

(71) Applicant: General Electric Company, Schenectady, NY (US)

(72) Inventors: Jiang Hsieh, Brookfield, WI (US); Saad Ahmed Sirohey, Pewaukee, WI (US); Roy A. Nilsen, Waukesha, WI (US); Suresh Narayanan Narayanan, Waukesha, WI (US); Guangzhi Cao, Madison, WI (US)

(73) Assignee: General Electric Company, Schenectady, NY (US)

( * ) Notice: Subject to any disclaimer, the term of this patent is extended or adjusted under 35 U.S.C. 154(b) by 133 days.

(21) Appl. No.: 14/484,544

(22) Filed: Sep. 12, 2014

(65) Prior Publication Data

US 2016/0078619 A1    Mar. 17, 2016

(51) Int. Cl.
*A61B 6/03* (2006.01)
*A61B 6/00* (2006.01)
(Continued)

(52) U.S. Cl.
CPC .............. *A61B 6/504* (2013.01); *A61B 6/032* (2013.01); *A61B 6/06* (2013.01); *A61B 6/481* (2013.01);
(Continued)

(58) Field of Classification Search
CPC ........... A61B 6/032; A61B 6/06; A61B 6/481; A61B 6/504; A61B 6/5205; A61B 6/542
(Continued)

(56) References Cited

U.S. PATENT DOCUMENTS

| 5,930,384 A | * | 7/1999 | Guillemaud | .......... | G06T 11/006 |
| | | | | | 250/363.04 |
| 6,373,920 B1 | * | 4/2002 | Hsieh | ..................... | A61B 6/507 |
| | | | | | 378/8 |

(Continued)

FOREIGN PATENT DOCUMENTS

| WO | 03041583 A2 | 5/2003 |
| WO | 03046797 A2 | 6/2003 |

(Continued)

OTHER PUBLICATIONS

C. A. Cuenod and D. Balvay. Perfusion and vascular permeability: Basic concepts and measurement in DCE-CT and DCE-MRI. Diagnostic and Interventional Imaging (2013) 94, 1187-1204.*

(Continued)

*Primary Examiner* — Allen C. Ho
(74) *Attorney, Agent, or Firm* — Dean D. Small; The Small Patent Law Group, LLC

(57) ABSTRACT

An imaging system includes a computed tomography (CT) acquisition unit and a processing unit. The CT acquisition unit includes an X-ray source and a CT detector configured to collect CT imaging data of an object to be imaged. The processing unit includes at least one processor operably coupled to the CT acquisition unit. The processing unit is configured to control the CT acquisition unit to collect at least one sample projection during rotation of the CT acquisition unit about the object to be imaged, compare an intensity of the at least one sample projection to an intensity of a reference projection, select a time to perform an imaging scan based on the comparison of the intensity of the at least one sample projection to the intensity of the reference projection, and control the CT acquisition unit to perform the imaging scan.

21 Claims, 14 Drawing Sheets

(51) Int. Cl.
  A61B 6/06 (2006.01)
  G06K 9/46 (2006.01)
  G06K 9/62 (2006.01)
  G06T 7/00 (2006.01)
  G06T 7/20 (2006.01)
  A61B 6/02 (2006.01)

(52) U.S. Cl.
  CPC ............... *A61B 6/486* (2013.01); *A61B 6/488* (2013.01); *A61B 6/507* (2013.01); *A61B 6/5205* (2013.01); *A61B 6/5217* (2013.01); *A61B 6/5252* (2013.01); *A61B 6/541* (2013.01); *A61B 6/542* (2013.01); *A61B 6/545* (2013.01); *G06K 9/4661* (2013.01); *G06K 9/6215* (2013.01); *G06T 7/0014* (2013.01); *G06T 7/20* (2013.01); *A61B 6/025* (2013.01); *G06T 2207/30048* (2013.01)

(58) Field of Classification Search
  USPC ........................................................ 378/8, 16
  See application file for complete search history.

(56) References Cited

U.S. PATENT DOCUMENTS

| | | | | |
|---|---|---|---|---|
| 6,512,807 B1 * | 1/2003 | Pohlman | ................ | A61B 6/481 378/19 |
| 6,745,066 B1 * | 6/2004 | Lin | ................ | A61B 6/481 378/4 |
| 6,876,720 B2 * | 4/2005 | Tsuyuki | ................ | A61B 6/032 378/4 |
| 6,888,914 B2 * | 5/2005 | Edic | ................ | A61B 6/032 378/4 |
| 6,891,918 B2 * | 5/2005 | Drummond | ............ | A61B 6/032 378/5 |
| 6,934,353 B2 * | 8/2005 | Wang | ................ | A61B 6/032 378/15 |
| 6,983,182 B2 * | 1/2006 | Mistretta | ................ | A61B 6/032 382/131 |
| 7,054,406 B2 * | 5/2006 | Ikeda | ................ | A61B 6/032 378/4 |
| 7,209,536 B2 * | 4/2007 | Walter | ................ | A61B 6/032 378/5 |
| 7,218,702 B2 * | 5/2007 | Mistretta | ................ | A61B 6/025 378/21 |
| 7,477,929 B2 * | 1/2009 | Klotz | ................ | A61B 6/481 600/419 |
| 7,545,901 B2 * | 6/2009 | Mistretta | ............... | G06T 11/006 378/4 |
| 7,627,078 B2 * | 12/2009 | Hsieh | ................ | A61B 6/032 378/19 |
| 7,684,536 B2 * | 3/2010 | Kudo | ................ | A61B 6/032 378/4 |
| 7,715,519 B2 * | 5/2010 | Tsukagoshi | ............ | A61B 6/032 378/4 |
| 7,715,522 B2 * | 5/2010 | Goto | ................ | A61B 6/032 378/16 |
| 7,756,242 B2 * | 7/2010 | Kudo | ................ | A61B 6/032 378/15 |
| 7,840,255 B2 * | 11/2010 | Ichihara | ................ | A61B 6/481 600/407 |
| 7,853,309 B2 * | 12/2010 | Ichihara | ................ | A61B 6/481 600/407 |
| 7,903,856 B2 * | 3/2011 | Pfister | ................ | A61B 5/02007 345/419 |
| 8,050,479 B2 * | 11/2011 | Hsieh | ................ | A61B 6/032 378/16 |
| 8,126,236 B2 * | 2/2012 | Harer | ................ | A61B 6/466 378/901 |
| 8,160,338 B2 * | 4/2012 | Ichihara | ................ | A61B 6/481 378/4 |
| 8,175,358 B2 * | 5/2012 | Weese | ................ | A61B 6/481 382/131 |
| 8,208,699 B2 * | 6/2012 | Hay | ................ | A61B 6/469 378/8 |
| 8,295,915 B2 | 10/2012 | Grasruck et al. | | |
| 8,428,694 B2 * | 4/2013 | Kalafut | ................ | A61B 6/507 382/128 |
| 8,447,009 B2 * | 5/2013 | Flohr | ................ | A61B 6/032 378/5 |
| 8,542,891 B2 * | 9/2013 | Yokota | ................ | A61B 6/12 378/98.11 |
| 8,605,977 B2 * | 12/2013 | Bruder | ................ | A61B 6/032 382/131 |
| 8,731,262 B2 * | 5/2014 | Rauch | ................ | G06T 7/2053 382/130 |
| 8,768,030 B2 * | 7/2014 | Bruder | ................ | A61B 6/032 378/10 |
| 8,768,031 B2 * | 7/2014 | Mistretta | ............... | A61B 6/4441 382/128 |
| 9,047,702 B2 * | 6/2015 | Schmitt | ................ | A61B 6/032 |
| 9,317,915 B2 * | 4/2016 | Boese | ................ | G06T 7/0012 |
| 9,427,201 B2 * | 8/2016 | West | ................ | A61B 6/466 |
| 2011/0069063 A1 | 3/2011 | Liao et al. | | |
| 2012/0181428 A1 | 7/2012 | Bert et al. | | |
| 2013/0279783 A1 | 10/2013 | Schmitt et al. | | |

FOREIGN PATENT DOCUMENTS

| | | |
|---|---|---|
| WO | 2012052901 A1 | 4/2012 |
| WO | 2012093364 A1 | 7/2012 |

OTHER PUBLICATIONS

Kyongtae T. Bae. Intravenous Contrast Medium Administration and Scan Timing at CT: Considerations and Approaches. Radiology: vol. 256: No. 1, Jul. 2010, 32-61.*
Masato Matsumoto et al. 3D-CT Arteriography and 3D-CT Venography: The Separate Demonstration of Arterial-Phase and Venous-Phase on 3D-CT Angiography in a Single Procedure. AJNR American Journal of Neuroradiology 26: 635-641, Mar. 2005.*
Search Report and Written Opinion from Corresponding PCT Application No. PCT/US2015/043584 dated Oct. 8, 2015; 10 pages.
Prevrhal et al, "CT angiographic Measurement of vascular blood flow velocity using projection data", 100 RSNA Radiology Dec. 2011.

* cited by examiner

Delay time = 14.5 seconds

Delay time = 16.5 seconds

Delay time = 18.5 seconds

SYSTEMS AND METHODS FOR IMAGING PHASE SELECTION FOR COMPUTED TOMOGRAPHY IMAGING

BACKGROUND OF THE INVENTION

The subject matter disclosed herein relates generally to systems and methods for computed tomography (CT) imaging, for example to systems and methods for perfusion studies using CT imaging.

In CT imaging, an X-ray source may be rotated around an object to obtain imaging information. X-rays from the source attenuated by the object may be collected or detected by a detector and used to reconstruct an image. Patient radiation dose from the X-ray source is a concern in clinical practice.

In conventional perfusion studies, a large number of scans may be acquired, or the time of exposure to X-rays may be relatively large, resulting in relatively high X-ray doses for perfusion exams relative to other types of CT exams. For example, in traditional CT perfusion exams, for each anatomical location-of interest a series of CT scans are taken on a patient sequentially over a period of time that covers the pre-contrast phase, contrast uptake phase, and contrast washout phase. The contrast uptake and washout phase information are retrieved by measuring the contrast in the artery and vein regions of interest in the series of reconstructed image volumes. There may be as many as 20 or more scans in total in one perfusion example. Therefore, the X-ray dose in traditional CT perfusion exams may be significantly higher than other types of CT exams.

Recently, some studies have indicated that CT perfusion studies may be accomplished using only three scans taken at appropriately selected phases, namely a pre-contrast phase, an arterial phase, and a delayed phase. Accordingly, if arterial and delayed phases can be efficiently estimated without requiring reconstructed images, most of the scans of current or traditional perfusion protocols may be eliminated. Elimination of many or most of the scans of current or traditional perfusion protocols my simplify the perfusion exams and save a significant amount of X-ray radiation dose to a patient. Or alternatively, even for traditional perfusion studies where a series of scans are collected, sampling intervals may be dynamically adjusted based on the phase of the contrast uptake. For example, the arterial phase may be sampled at a higher frequency than the washout phase. However, the identification of the phases (e.g., arterial phase) or portions thereof (e.g., onset of arterial phase, transition from arterial phase to washout phase) using certain known approaches is estimated before a perfusion study is initiated. These estimations often suffer from inaccuracy, due, for example, to differences between patients.

BRIEF DESCRIPTION OF THE INVENTION

In one embodiment, an imaging system is provided that includes a computed tomography (CT) acquisition unit and a processing unit. The CT acquisition unit includes an X-ray source and a CT detector configured to collect CT imaging data of an object to be imaged. The X-ray source and CT detector are configured to be rotated about the object to be imaged and to collect a series of projections of the object as the X-ray source and CT detector rotate about the object to be imaged. The processing unit includes at least one processor operably coupled to the CT acquisition unit. The processing unit is configured to control the CT acquisition unit to collect at least one sample projection during rotation of the CT acquisition unit about the object to be imaged, compare an intensity of the at least one sample projection to an intensity of a reference projection, select a time to perform an imaging scan based on the comparison of the intensity of the at least one sample projection to the intensity of the reference projection, and control the CT acquisition unit to perform the imaging scan.

In another embodiment, a method is provided that includes obtaining, with a computed tomography (CT) acquisition unit, at least one sample projection of CT imaging information during rotation of the CT acquisition unit about an object to be imaged. The method also includes comparing an intensity of the at least one sample projection to an intensity of a reference projection. Further, the method includes selecting a time to perform an imaging scan based on the comparison of the intensity of the at least one sample projection to the intensity of the reference projection. Also, the method includes controlling the CT acquisition unit to perform the imaging scan based on the selected time.

In another embodiment, a tangible and non-transitory computer readable medium is provided that includes comprising one or more computer software modules that are configured to direct one or more processors to obtain, via a computed tomography (CT) acquisition unit, at least one sample projection of CT imaging information during rotation of the CT acquisition unit about an object to be imaged. The one or more computer software modules are also configured to direct the one or more processors to compare the intensity of the at least one sample projection to an intensity of a reference projection. Further, the one or more computer software modules are also configured to direct the one or more processors to select a time to perform an imaging scan based on the comparison of the intensity of the at least one sample projection to the intensity of the reference projection. Also, the one or more computer software modules are configured to direct the one or more processors to control the CT acquisition unit to perform the imaging scan based on the selected time.

DETAILED DESCRIPTION OF THE INVENTION

Figure 1:
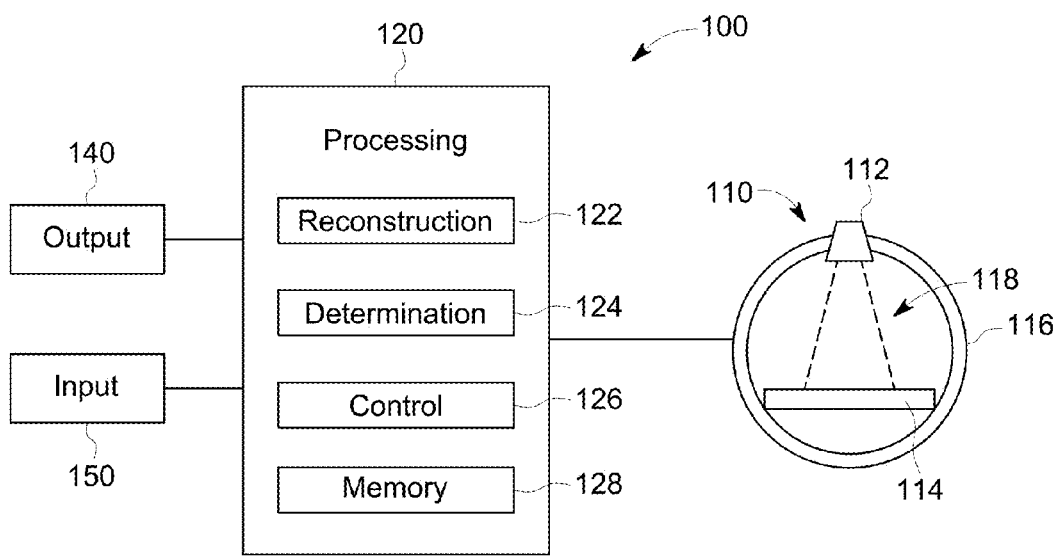
FIG. 1 is a schematic block diagram illustrating an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for identifying a time to perform an imaging scan, for example to identify a particular phase (or portion thereof) of a perfusion study and to perform an imaging scan at a time corresponding to the particular phase (or portion thereof). For example, an aspect or characteristic of one or more sample projections (e.g., a total intensity for soft tissue) may be compared with an aspect or characteristic of a reference projection (or baseline projection), used to identify a perfusion phase (or portion thereof), and used to select a time for performance of an imaging scan or to trigger performance of an imaging scan. As used herein, an imaging scan may be understood as an acquisition of imaging information that is sufficient to provide a diagnostically useful image (e.g., an image having sufficient resolution for diagnostic uses). Sample projections or monitor images, and reference or baseline projections as discussed herein include imaging information (e.g., CT imaging information), but may not include enough imaging information to provide a diagnostically useful image, and are not imaging scans. For example, an imaging scan may include acquisition of information over a complete rotation of a CT acquisition unit, or a relatively large portion of a rotation (e.g., half or nearly half of a rotation). In contrast, a sample projection or a reference projection may be acquired over a relatively small range or time of rotation of a CT acquisition unit, such as $\frac{1}{1000}$ of a rotation, or less than one degree.

In various embodiments, perfusion phases are estimated using one or more projection views or sample projections over a number of rotations (either consecutive or non-consecutive rotations in various embodiments), and automatically triggering performance of an imaging scan at pre-specified or predetermined phases (or portions of phases). For example, a correlation between processed projection information and vessel intensity in perfusion exams may be established. Phase information, such as timing or onset of arterial and venous (or washout, or delayed) phases may be estimated in real time using one or a few sample projections for each of a group of gantry rotations while the gantry is continuously rotating, with full rotation scans (or imaging scans of more or less than a full rotation) taken only when pre-specified or predetermined phases (or portions thereof) are reached. Further, information derived from a projection-based phase estimation, such as the rising and decay slopes of the arterial curve, and the rising and decay slopes of the venous curve, may be used to model cardiac output of a patient.

For example, in various embodiments, phase estimation and scan automation using projection data may be realized through steps of view selection/optimization, bone removal (and/or other high density material), and intensity calculation and comparison.

In one example embodiment, during a first rotation of a gantry of a CT acquisition system, for example before administration of a contrast agent into an object to be imaged (e.g., before injection of contrast agent into a patient), a reference position is selected and a reference projection acquired. For example, for a scan of the head, to reduce the impact of head motion, a projection at 3:00 and/or 9:00 positions (e.g., views oriented toward a side or profile of the head) may be utilized. For body scans, views at 12:00 or 6:00 (e.g., views oriented toward a front or back of a patient being imaged) may be utilized.

A bone removal step may next be applied to the reference projection, for example to reduce the impact of motion. The bone removal (which may also be used to remove other high density information such as information corresponding to metallic implants) may be performed using image processing methods such as erosion, as bones may be located on the periphery of a head or body portion to be imaged. For neuro perfusion, bone removal may be performed with "skull recognition" software to remove only the bony structure of the skull while maintaining the presence of soft tissue. For body perfusion, for example a liver perfusion study, the spine and ribs may be removed with generally similar recognition software. Further still, if a dual energy projection is obtained, material decomposition may be utilized to remove the bones without extensive image processing.

Continuing with the example embodiment, after the acquisition of the reference projection, for a number of rotations after the rotation for which the reference projection was obtained, one or a few projections are collected at or near the same view angle as the reference projection. For example, if multiple views or projections are available in a neuro perfusion study, a view in which the orientation of the projected head is closest to that in the reference projection may be selected for further processing (e.g., removal of bone, determination of contrast intensity). The selection of the orientation closest to the reference projection may be based on an assumption that movement of the head is primarily rotational in nature. It may be noted that, for body scans, additional shift or affine transformation may be performed to eliminate or reduce the impact of respiratory motion, for example. After a projection is selected, the projection may be slightly rotated in plane or otherwise adjusted to even more closely match the orientation of the reference projection. The selection and/or adjustment of a projection may be understood as view optimization as used herein. Next, a similar bone removal as performed with the reference projection may be performed with the optimized view or projection.

For each projection acquired or selected as discussed above, the current projection (e.g., with bone removed) may next be compared to the reference projection. For example, a difference between the current bone-removed projection and the sample projection may be taken. The resulting difference projection contains the contrast distribution in the organ-of-interest or region-of-interest. The sum of the intensities of the difference projection for a rotation may be used as a contrast intensity measure for that particular rotation. By monitoring a curve of the contrast intensity measures for a number of sample projections (e.g., selected or acquired projections for a series of consecutive rotations), the timing for performance of imaging scans may be determined (e.g., automatically or autonomously determined by one or more processing units monitoring the contrast intensity measures). For example, in a three-phase perfusion approach, a CT imaging scan may be triggered when the slope of the rising intensity curve is significantly reduced (e.g., near the end of an increase in intensity) to provide an arterial phase image. Similarly, a CT imaging scan may be triggered when the rate of change for a washout curve becomes small to provide a venous or washout phase image. The particular values for triggering the imaging scans may be experimentally determined or determined as part of a clinical study, and may be varied or tailored for a particular application, procedure, and/or patient. It may be noted that in some embodiments, more than one sample projection per rotation may be obtained (e.g., two sample projections at opposed rotation positions, such as at 0 degrees and 180 degrees, or at 90 degrees and 270 degrees), and that in some embodiments, a sample projection may not be acquired for each and every rotation (e.g., a sample projection may be acquired for every other rotation). As the sample projections are obtained, if a target phase is not reached (e.g., an intensity value for a given sample projection and/or slope associated with the intensity value does not satisfy a threshold to trigger an imaging scan), the gantry may continue to rotate and one or more additional sample projections may be obtained. If a target phase is reached, a CT imaging scan may be performed. After performing the imaging scan, if additional target phases exist for which subsequent imaging scans are desired, additional sample projections may be obtained until the final desired target phase has been imaged.

In various embodiments, by smoothly fitting the intensity measures for a number of sample projections over time, a contrast intensity curve may be plotted over time. Optionally, high- and/or low-pass filters may be applied to difference projection data to separate contrast in arteries, veins, and the rest of an organ. Information such as rate of contrast intensity change (and accordingly, rate of contrast uptake change) and intensity peak may be obtained using a contrast intensity curve. Based on the information obtained via the contrast intensity curve, perfusion phases (e.g., timing of onset of perfusion phases) and patient cardiac output may be estimated.

Various embodiments provide improved imaging. A technical effect of at least one embodiment includes reduced number of scans and reduced radiation dose during perfusion studies. A technical effect of at least one embodiment includes improved selection of timing for performance of imaging scans during perfusion studies. A technical effect of at least one embodiment is to provide a dynamic trigger for imaging scans during perfusion studies instead of a fixed trigger. A technical effect of at least one embodiment includes providing determination of cardiac output in conjunction with a CT perfusion study. A technical effect of at least one embodiment includes reduction of delay between reaching a desired phase or portion thereof and triggering of an imaging scan.

FIG. 1 illustrates an imaging system 100 in accordance with an embodiment. The imaging system 100 may be configured, for example, to perform computed tomography (CT) scanning of an object, such as a human or animal patient (or portion thereof), such as CT scanning for a perfusion study. The imaging system 100 includes a CT acquisition unit 110 and a processing unit 120. Generally, the CT acquisition unit 110 is configured to acquire projection data or imaging data (e.g., CT data or CT imaging information), and the processing unit 120 is configured to reconstruct images using the data acquired by the CT acquisition unit 110. It may be noted that various embodiments may include additional components, or may not include all of the components shown in FIG. 1 (for example, various embodiments may provide sub-systems for use with other sub-systems to provide an imaging system). Further, it may be noted that certain aspects of the imaging system 100 shown as separate blocks in FIG. 1 may be incorporated into a single physical entity, and/or aspects shown as a single block in FIG. 1 may be shared or divided among two or more physical entities.

The depicted CT acquisition unit 110 includes an X-ray source 112 and a CT detector 114. (For additional information regarding example CT systems, see FIG. 12 and related discussion herein.) The X-ray source 112 and the CT detector 114 (along with associated components such as bowtie filters, source collimators, detector collimators, or the like (not shown in FIG. 1)) may rotate about a central axis of a bore of a gantry 116 of the system 100.

Generally, X-rays from the X-ray source 112 may be guided to an object to be imaged through a source collimator and bowtie filter. The object to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter module may be configured to absorb radiation from the X-ray source 112 to control distribution of X-rays passed to the object to be imaged.

X-rays that pass through the object to be imaged are attenuated by the object and received by the CT detector 114 (which may have a detector collimator associated therewith), which detects the attenuated X-rays and provides imaging information to the processing unit 120. The processing unit 120 may then reconstruct an image of the scanned portion of the object using the imaging information (or projection information) provided by the CT detector 114. The processing unit 120 may include or be operably coupled to the output unit 140, which in the illustrated embodiment is configured to display an image, for example, an image reconstructed by the processing unit 120 using imaging information from the CT detector 114. The depicted input unit 150 is configured to obtain input corresponding to a scan to be performed, with the processing unit 120 using the obtained input to determine one or more scan settings (e.g., tube voltage, tube current, scanning rotation speed, or the like). The input unit 150 may include a keyboard, mouse, touchscreen or the like to receive input from an operator, and/or may include a port or other connectivity device to receive input from a computer or other source.

In the illustrated embodiment, the X-ray source 112 is configured to rotate about the object. For example, the X-ray source 112 and the CT detector 114 may be positioned about a bore 118 of the gantry 116 and rotated about the object to be imaged. As the X-ray source 112 rotates about the object during an imaging scan, X-rays received by the CT detector 114 during one complete rotation provide a 360 degree view of X-rays that have passed through the object. Other imaging scanning ranges may be used in alternative embodiments. The CT imaging information may be collected as a series of views that together make up a rotation or portion thereof. Each view or projection may have a view duration during which information (e.g., counts) is collected for the particular view. The view duration for a particular view defines a CT information acquisition period for that particular view. For example, each rotation may be made up of about 1000 views or projections, with each view or projection having a duration or length of about $\frac{1}{1000}$ of a complete rotation. The X-ray source 112 may be turned on and off to control the acquisition time. For example, to perform an imaging scan of a complete rotation, the X-ray source 112 may be turned on at a particular rotational position of the gantry 116 and turned off when the X-ray source 112 returns to the particular rotational position after a complete rotation. To perform an acquisition for a single view (e.g., for a reference projection or sample projection as discussed herein), the X-ray source 112 may be turned on for only a portion of the rotation corresponding to the single view. For example, in embodiments having 1000 views or projections per rotation, and with the gantry rotating at a constant speed, the X-ray source 112 may be left on for $\frac{1}{1000}$ of the time of a complete rotation to acquire a single view or projection of CT information. A blanking interval for may separate a first view or projection from the next view or projection in the series.

As indicated herein, the processing unit 120 is configured to control various aspects of the acquisition units and/or to reconstruct an image using information obtained via the acquisition units. For example, the processing unit 120 may be configured to reconstruct a CT image using information collected by the CT acquisition unit 110.

The depicted processing unit 120 is operably coupled to the input unit 150, the output unit 140, and the CT acquisition unit 110. The processing unit 120, for example, may receive information regarding a scan from the input unit 150 that may be utilized in determining scanning parameters to be used in acquiring CT imaging information. As another example, the processing unit 120 may receive imaging data or projection data from the CT detector 114. As one more example, the processing unit 120 may provide control signals to one or more aspects of the CT acquisition unit 110, such as the X-ray source 112 and CT detector 114. The processing unit 120 may include processing circuitry configured to perform one or more tasks, functions, or steps discussed herein. It may be noted that "processing unit" as used herein is not intended to necessarily be limited to a single processor or computer. For example, the processing unit 120 may include multiple processors and/or computers, which may be integrated in a common housing or unit, or which may distributed among various units or housings.

Figure 2:
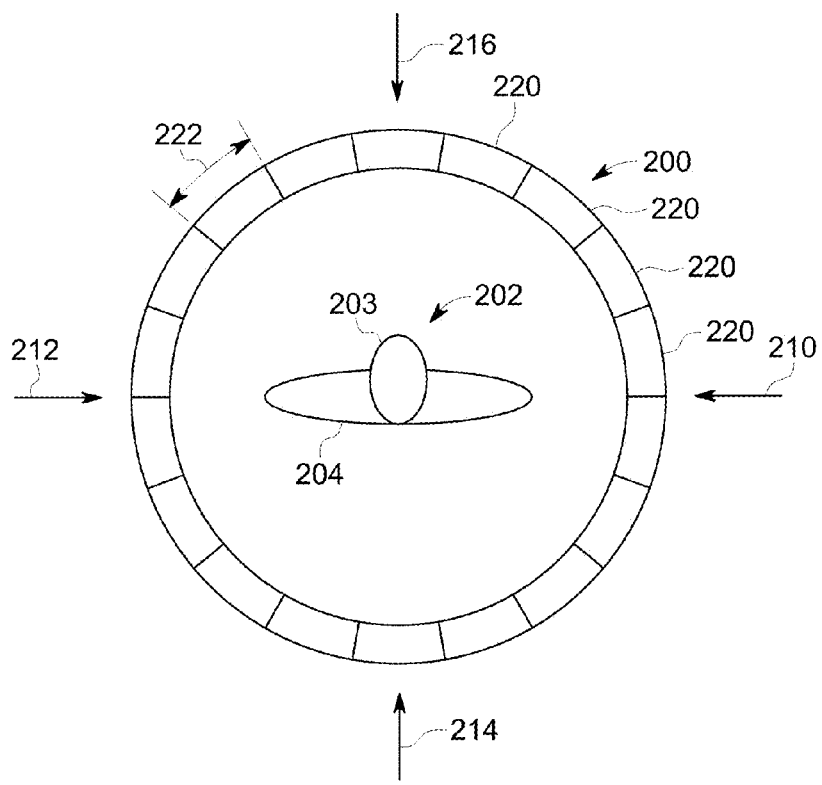
FIG. 2 illustrates different view angles or projections in a rotation in accordance with various embodiments.

The depicted processing unit 120 is configured to control the CT acquisition unit 110 (e.g., by controlling the activation and deactivation of the X-ray source 112) to collect CT information for reference projections and sample projections, as well as to collect CT imaging information during an imaging scan. In various embodiments, the processing unit 120 may control the CT acquisition unit 110 to first obtain a reference projection for an object to be imaged before uptake of contrast agent (e.g., before, during or shortly after injection of a contrast agent and before the contrast agent has a noticeable effect on the imaged portion of the object). Further, the processing unit 120 may be configured to control the CT acquisition unit 110 to collect at least one sample projection during rotation of the CT acquisition unit 110 about the object 102 to be imaged, to compare an intensity of the at least one sample projection to an intensity of the reference projection, to select a time to perform an imaging scan based on the comparison of the intensity of the at least one sample projection to the intensity of the reference projection (e.g., to trigger an imaging scan when an intensity or intensity profile reaches or satisfies a threshold), and to control the CT acquisition unit to perform the imaging scan, FIG. 2 illustrates examples of positions of views or projections about an object to be imaged within a single rotation. It should be noted that the angular ranges covered by each view or projection is shown for the purposes of clarity of illustration. As seen in FIG. 2, a series of views 220 or projections make up a complete rotation of a gantry 200, with each view 220 having a duration 222. In practice, each view 220 or projection may cover a substantially smaller angular range than shown in FIG. 2. For example, in some embodiments, there may be about 1,000 views or projections available per rotation, with each view or projection covering about $\frac{1}{1000}$ of a complete rotation, or about 0.3 degrees. In the example illustrated in FIG. 2, an object 202 to be imaged (e.g., human patient) includes a head 203 and a torso 204. The head 203 and torso 204 are examples of portions of the object 202 for which different view angles may be employed to obtain reference and sample projections.

For example, as seen in FIG. 2, a first lateral view angle 210 or azimuth views the object 202 from a first lateral side, while a second lateral view angle 212 or azimuth views the object 202 from a second lateral side opposite the first lateral side. Views or projections taken from the first lateral view angle 210 and/or the second lateral view angle 212 may be desirable for studies relating to the head 203 of the patient. For example, structures of the head 203 may be more aligned from the front to back of the head than from side to side, so that views from the side (e.g., the first lateral view angle 210 and/or the second lateral view angle 212) of the head 203 are less likely to be affected by motion of the head that may occur during acquisition of CT information than from other view angles. As another example, a posterior view angle 214 or azimuth views the object 202 from beneath or from the back of the object 202, and an anterior view angle 216 or azimuth views the object 202 from above or from the front of the object 202. Views or projections taken from the posterior view angle 214 and/or the anterior view angle 216 may be desirable for studies relating to the torso 204 of the patient. For example, movement of the torso 204 due to breathing may have less effect on imaging information when viewed from the front or back of the torso 204 than when viewed from the side, so that views from the posterior view angle 214 and/or the anterior view angle 216 of the torso 204 are less likely to be affected by motion of the torso 204 that may occur during acquisition of CT information than other view angles.

Accordingly, selection of a lateral view angle when performing a perfusion study of the head to be used for reference and sample projections may provide improved accuracy or reliability in the determination of perfusion phase information (e.g., identifying a perfusion phase or portion thereof and performing a CT imaging scan corresponding to the perfusion phase), and selection of a posterior or anterior view angle for reference and sample projections when performing a perfusion study of the torso may provide improved accuracy or reliability in the determination of perfusion phase information. Thus, the view angle for the reference projection and/or sample projections may be selected or determined based on the type of exam (e.g., portion of anatomy being imaged) to improve accuracy or reliability (e.g., reduce the effect of motion on the reference and sample projections). In various embodiments, sample projections may be selected at or near the same view angle as used for the reference projection for consistency and reliability of comparison between the reference projection and sample projections.

Figure 3:
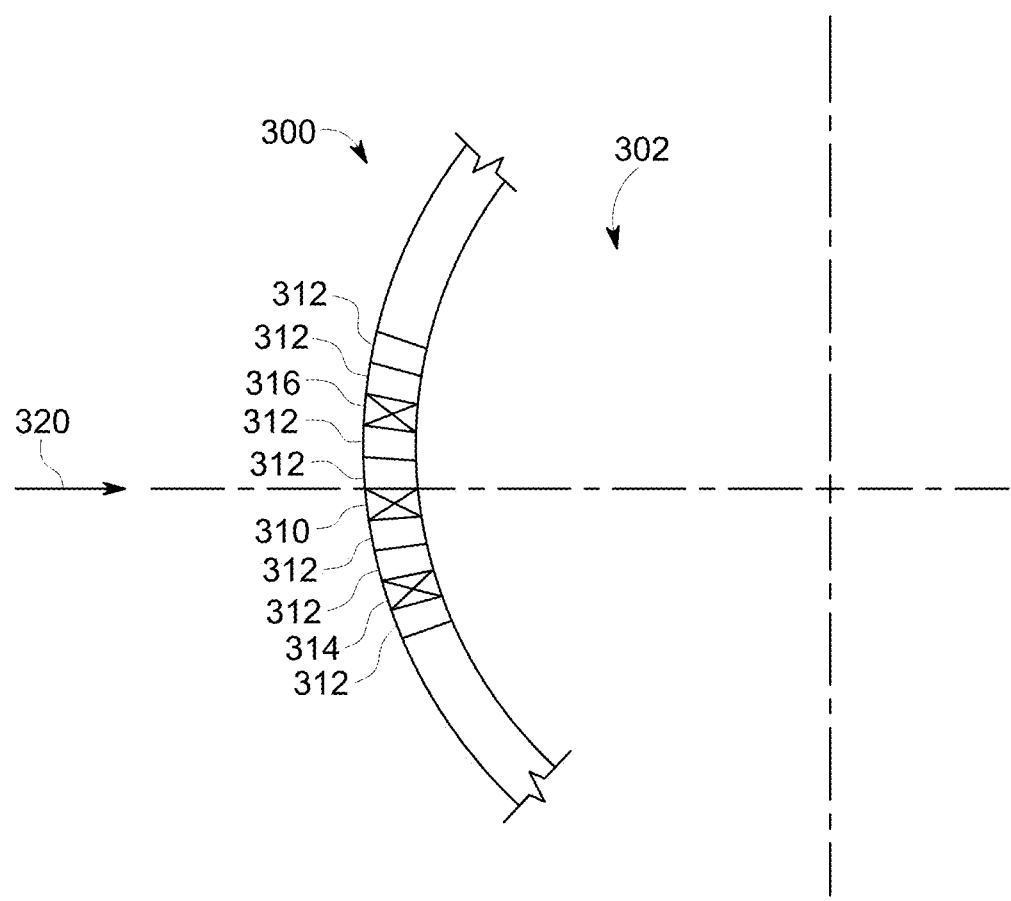
FIG. 3 illustrates candidate views over a portion of a rotation in accordance with various embodiments.

In some embodiments, the processing unit 120 is configured to collect plural candidate projections during rotations (e.g., consecutive rotations) of the CT acquisition unit 110, and for each rotation to select a sample projection to be compared with the reference projection. The sample projection may be selected from among the candidate projections based on similarity to the reference projection (e.g., based on a comparison of one or more aspects or characteristics of the candidate projections to the reference projection). FIG. 3 shows an example of a group of candidate projections disposed around a bore 302 of a gantry 300 in accordance with various embodiments. For the example shown in FIG. 3, only a portion of the gantry 300 and only a portion of the views or projections of a rotation are shown for ease and clarity of illustration. Further, for the example shown in FIG. 3, a reference projection may be understood to have been previously taken at or near view angle 320.

In the example depicted in FIG. 3, there are three candidate projections or views for which CT information is acquired (e.g., the X-ray source is activated when the gantry is at positions corresponding to the candidate projections or views). In FIG. 3, a first candidate view 310 (for which a corresponding first candidate projection may be obtained), a second candidate view 314 (for which a corresponding second candidate projection may be obtained), and a third candidate view 316 (for which a corresponding third candidate projection may be obtained) are shown. As seen in FIG. 3, the first candidate view 310 is located at or near a lateral side of the gantry 300, with the second candidate view 314 located counter-clockwise from the first candidate view 310 and the third candidate view 316 located clockwise from the first candidate view 310. Thus, if the X-ray source 112 and CT detector 114 are rotating clockwise around the gantry 300, a projection for the second candidate view 314 will be the first candidate projection acquired, a projection for the first candidate view 310 will be the next candidate projection acquired, and a project for the third candidate view 316 will be the last candidate projection acquired.

The candidate views in FIG. 3 are spaced apart from neighboring candidate views by two non-candidate views 312 (e.g., views for which an X-ray source is not activated or for which a corresponding candidate projection is otherwise not acquired). The candidate projections may be acquired by turning an X-ray source 112 on and off at appropriate times as an X-ray source 112 and CT detector 114 rotate about an object to be imaged. As the X-ray source 112 may be activated only for the relatively short duration of the candidate projections (which form a small percentage of the total available views or projections for a rotation), the total radiation dosage for the candidate projections may be substantially smaller than the dosage for an imaging scan. In FIG. 3, the second candidate view 314 and the third candidate view 316 are equally spaced from the first candidate view 310 and disposed on opposite sides of the first candidate view 310, with the first candidate view 310 located at the same position for which a reference projection was previously acquired. It may be noted that the particular positions of the candidate and non-candidate views of FIG. 3 are provided by way of example, and that other arrangements or configurations of candidate and non-candidate views may be utilized in other embodiments. For example, different spacings between candidate views may be employed, the candidate views may be immediately adjacent instead of spaced apart by non-candidate views, fewer or more candidate views may be acquired, different positions along the gantry 300 may be used for candidate views (e.g., candidate views may be additionally or alternatively provided at an additional lateral side, candidate views may be used at anterior and/or posterior view angles), or the like.

With the candidate projections acquired, the particular sample projection (or projections) to be compared with the reference projection to determine a timing of performing an imaging scan may be selected from among the candidate projections. For example, a group of candidate projections may be acquired for each rotation of the gantry 300, and a sample projection for each rotation selected from among the candidate projections acquired for that particular rotation. It may be noted that the sample projection most similar to the reference projection may be taken from a different view angle than the reference projection, for example due to movement of a patient after the reference projection is acquired. Accordingly, sample projections may be acquired on either side of the view angle from which the reference projection was acquired in various embodiments. The sample projection to be used may be selected from among the candidate projections based on similarity to one or more characteristics or aspects of the reference projection. For example, a correlation between the reference projection and each candidate projection may be determined, and the candidate projection with the highest correlation selected as the sample projection. As another example, a difference between the reference projection and each candidate projection may be determined, and the candidate projection with the lowest difference selected as the sample projection. It may be noted that the comparison of candidate projections to the reference projection may be based on different criteria or performed using different techniques than the comparison of the sample projection to reference projection. For example, as discussed herein, CT information corresponding to bones or other high density structures may be removed from the projections before comparing the selected sample projection to the reference projection. However, when identifying the candidate projection most similar to the reference projection, CT information corresponding to bones or other high density structures may be utilized. For example, CT information corresponding to bones may provide information that is useful for determining similarity of projections (e.g., similarity of effective view angle to object), while CT information corresponding to bones may not be useful for comparing intensities caused by perfusion uptake, as uptake of contrast agent in bones is relatively low, and CT information from bones may dilute, dominate, or overwhelm information from soft tissue that provides more information regarding uptake of contrast agent.

Returning to FIG. 1, in the illustrated embodiment, the processing unit 120 includes a reconstruction module 122, a determination module 124, a control module 126, and a memory 128. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein.

The depicted reconstruction module 122 is configured to reconstruct one or more images using imaging or projection data acquired from the CT detector 114. For example, the reconstruction module 122 may receive imaging information from the CT detector 114 taken over a number of views (e.g., for a full rotation or portion thereof, or for a number of rotations taken at different positions along the length of an object to be imaged) and reconstruct an image used for diagnostic purposes.

In the illustrated embodiment, the determination module 124 is configured to receive information from the CT acquisition unit 110 (e.g., CT information for a reference projection, candidate projections, and/or one or more sample projections) and/or the input unit 150 (e.g., information describing or corresponding to a patient, procedure, or scanning parameters) and to determine, for example, a time at which an imaging scan is to be performed. For example, the determination module 124 may determine an intensity for the reference projection and for one or more sample projections, and compare the intensities. The determination module 124 may take a difference between a sample projection and a reference projection to provide a difference projection that corresponds to the contrast distribution in a region of interest. When a sample projection is acquired having an intensity value relative to the intensity value for the reference projection that meets or satisfies a criteria such as a threshold, the determination module 124 may trigger or implement an imaging scan to be performed by the CT acquisition unit 110. The imaging scan may be triggered immediately or as soon as possible (e.g., there may be a lag between the triggering and the actual start of the imaging scan, for example due to time required to process information and/or activate the X-ray source 112), or there may be a delay between the detection of satisfaction of a threshold. For example, a peak intensity or onset of arterial phase may be experimentally determined to occur about 0.5 seconds after a certain threshold is reached. The processing unit 120 may then be configured to implement an imaging scan about 0.5 seconds after satisfaction of the threshold. Further, in some embodiments, the determination module 124 may select a sample projection (for which an intensity will be determined and compared to the reference projection) from among a group of reference projections for a given rotation, as discussed herein, for example, in connection with the example provided in FIG. 3.

Figure 4:
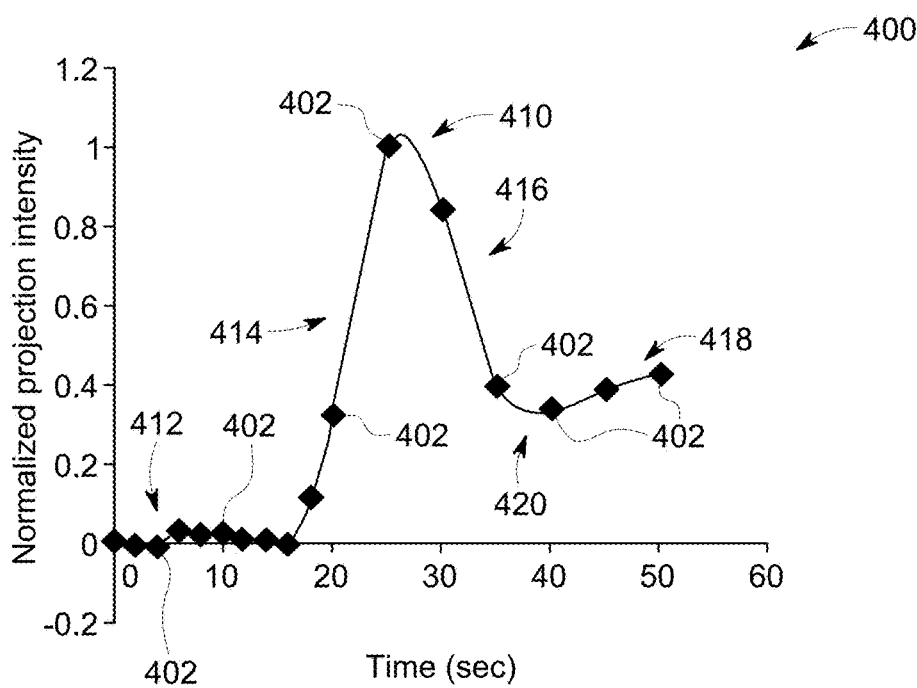
FIG. 4 illustrates a projection intensity curve in accordance with various embodiments.

In various embodiments, the determination module 124 may determine one or more times to trigger or implement an imaging scan based on an amplitude and/or a slope of a curve corresponding to intensities of sample projections acquired over a series of rotations. In various embodiments, a difference projection as described herein may be used to generate the intensity measures for each of the sample projections. FIG. 4 illustrates a curve 400 of normalized intensities (e.g., normalized with respect to a determined intensity of a reference projection) for sample projections taken from a number of rotations of a CT acquisition system. In FIG. 4, each data point 402 corresponds to a normalized intensity for a particular rotation, with the timing of each rotation identified in seconds along the horizontal axis. In the illustrated embodiment, the intensity values are shown as normalized relative to the reference projection intensity, but other configurations of curve or relationship between intensities (or other parameter) may be used in other embodiments.

As seen in FIG. 4, the curve 400 includes a first portion 412, a second portion 414, a third portion 416, and a fourth portion 418. The first portion 412 has a relatively flat slope with intensities similar to the intensity of the reference projection (e.g., normalized to a value of about zero), and represents the time from the first introduction of the contrast agent into a patient or the time from the acquisition of the reference projection (which may occur at or near the same time). During the first portion 412, significant uptake of the contrast agent into a region of interest to be imaged has not yet commenced. In some embodiments, a pre-contrast imaging scan may be performed at or about the time of introduction of contrast agent and before substantial or significant uptake of the contrast agent.

At about 16 seconds in the depicted example, uptake of the contrast agent begins to increase and become significant or substantial, resulting in a sharp positive slope and increasing uptake values for the second portion 414. The steepness of the slope may correspond to cardiac output, with higher cardiac outputs resulting in generally higher slope. The slope of a portion of the second portion 414 and/or an intensity value encountered along the second portion 414 may be used to predict (e.g., based on experimental studies or calibration studies) the onset of the arterial phase at 410, with an imaging scan triggered to be performed at or near a time corresponding to the point 410 of the curve 400 to provide an arterial phase image. In some embodiments, when the curve 400 reaches a local or absolute maximum (e.g., when the slope of the curve 400 is zero and/or switches from positive to negative), an arterial phase imaging scan may be triggered. As the scan may be triggered after the point 410 is reached, the scan may not performed precisely at the onset of the arterial phase or at the peak of intensity, but may be close enough to provide a clinically useful imager representative of the arterial phase of uptake of contrast agent.

After point 410, during the third portion 416 of the curve 400, the curve 400 descends to minimum at about 39 seconds to point 420 which is at a minimum at about point 420, which represents the onset of the venous (or washout or delay) phase in the illustrated embodiment, which is shown as the fourth portion 418 of the curve 400. Based on the slope and/or an intensity value during the third portion 416, an imaging scan may be implemented or triggered (e.g., by the processing unit 120) to be performed at or near the point in time when the curve 400 is at point 420 corresponding to the venous phase of uptake. Optionally, in some embodiments, when the curve 400 reaches a local or absolute minimum (e.g., when the slope of the curve 400 is zero and/or switches from negative to positive), a venous phase imaging scan may be triggered. For the illustrated example, a pre-uptake imaging scan may be performed at or near a time of zero seconds in the first portion 412, an arterial phase imaging scan may be performed at or near the point 410, and a venous phase imaging scan may be performed at or near the point 420.

In various embodiments, more or fewer imaging scans may be performed. For example, a pre-uptake imaging scan may be omitted in some embodiments. In some embodiments, more than one scan may be taken during the arterial phase and/or more than one scan taken during the venous phase. In embodiments in which multiple imaging scans are performed per phase, the identification of phase may be used to determine an imaging scan frequency. For example, more imaging scans (or more frequent imaging scans) may be performed during an arterial phase (e.g., the third portion 416) than during a venous or washout phase (e.g., the fourth portion 418).

Thus, in various embodiments, an imaging scan may be dynamically triggered based on information from the patient being imaged at the time of imaging information acquisition, in contrast to using an estimated delay from contrast agent injection for collection of imaging scans, which may not fully account for differences between patients or times of acquisition, and thus provide an inaccurate or unreliable estimate of the occurrence of phases (e.g., arterial, venous) of an uptake cycle. Further still, in some embodiments, the slope of the curve 400 may be monitored and used to select an appropriate threshold or criteria for triggering performance of an imaging scan. For example, when a relatively high slope for the second portion 414 is determined, a relatively high threshold (slope and/or amplitude) may be used to trigger an arterial phase imaging scan. When a relatively low slope for the second portion 414 is determined, a relatively low threshold (slope and/or amplitude) may be used to trigger an arterial phase imaging scan. When an intermediate slope for the second portion 414 is determined, an intermediate threshold (slope and/or amplitude) may be used to trigger an arterial phase imaging scan. The particular values of slopes and/or other thresholds, values of thresholds, and times to trigger relative to reaching or satisfying a threshold may be determined experimentally or using archived records to suit a particular application.

In some embodiments, the determination module 124 (and/or other aspect or portion of the processing unit 120) may process CT information and/or projections (e.g., reference projections, sample projections) before comparing one or sample projections with the reference projection (e.g., comparing intensities of the one or more sample projections and reference projection). For example, CT information corresponding to bone and/or other high density materials (e.g., metallic implants) may be removed from the reference projection and sample projections before determining intensities for comparison. Bone and/or other high density materials or structures such as metallic implants may provide little or no useful information regarding uptake, while accounting for a relatively large percentage of overall intensity or other imaging characteristic or aspect. Bone may produce a relatively large signal, and problems or issues caused by motion of a bone may overwhelm or drown out changes in intensity due to uptake in soft tissues. Accordingly, changes in uptake may be more accurately or reliably analyzed by removing some or all of the CT information in a given projection due to bone or other high density structures. As one example, erosion and/or dilation may be performed to remove CT information corresponding to bone and/or other high density structures, or, as another example, dual energy material identification and removal techniques may be used to remove CT information corresponding to bone and/or other high density structures in reference and sample projection before comparing intensities.

In some embodiments, the determination module 124 (or other aspect of the processing unit 120) may identify a vessel of interest and/or other structure in a region of interest, and the projection intensity for the vessel of interest and/or other structure may be compared between the reference projection and the sample projections, instead of comparing intensities for an entire region of interest. For example, a vascular structure, such as one or more large and identifiable arteries, may be identified and corresponding intensities for the vascular structure for the reference and sample projections may be compared. Utilizing a particular vascular structure for the projection intensity comparisons may provide a more accurate or reliable intensity curve (e.g., curve 400) and better accuracy in determining uptake phase (or portion thereof) than utilizing an entire region of interest or entire organ for projection intensity comparisons. However, it may also be noted that use of a particular vascular structure for the projection intensity comparisons may require additional time or computational resources, and/or be more susceptible to effects of motion than using an entire organ, for example. Accordingly, the particular portion used for the projection intensity comparisons may be selected based on the conditions or circumstances of a particular application. In some embodiments, the determination module may identify an amount of motion and utilize an entire organ for intensity comparisons when the amount of motion is relatively high, and utilize a particular vascular structure or structures when the amount of motion is relatively low.

Figure 5:
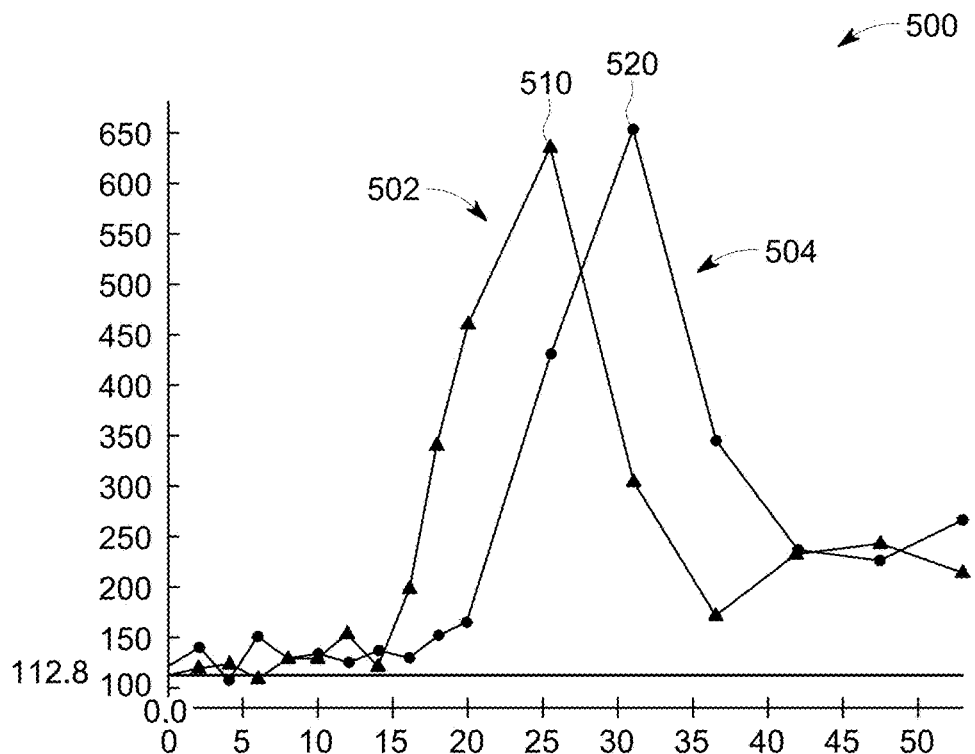
FIG. 5 illustrates a projection intensity plot.

It may be noted that, in various embodiments, triggering points for imaging scans may be identified using more than one intensity curve. FIG. 5 shows uptake curves for arterial structures and venous structures. As seen in FIG. 5, the intensity plot 500 includes an arterial intensity curve 502 that peaks at 510, and a venous intensity curve 504 that peaks at 520. The arterial intensity curve 502 may describe normalized intensity values for an artery collected at various sample projections relative to a reference projection, and the venous intensity curve 504 may describe normalized intensity values for a vein collected at various sample projections relative to a reference projection, One or more imaging scans for arterial phase imaging may be triggered based on intensity slope and/or amplitude of the arterial intensity curve 502, while one or more imaging scans for venous or washout phase imaging may be triggered based on intensity slope and/or amplitude of the venous intensity curve 504.

Further still, in some embodiments, the determination module 124 (and/or other aspect of the processing unit 120) may also determine cardiac output for a patient being imaged based on the slope of rise between the pre-uptake and arterial phases (e.g., the slope of all or a part of the second portion 414 of the curve 400). Generally, a steeper slope is indicative of a relatively higher output, and a shallower slope is indicative of a relatively lower output. Experimentally determined relationships or relationships determined in clinical studies between slope, amplitude and cardiac output may be utilized (e.g., in the form of an equation or look-up table) to determine cardiac output. One or more of slope or amplitude of the intensity curve may be used as an input to an experimentally determined relationship to provide the cardiac output as an output.

By using just one (or a relatively low number) of images for each phase, diagnostically useful images for a perfusion study may be obtained without the high dosage associated with traditional or conventional perfusion studies. While the use of fewer images may be more appropriate in some circumstances for qualitative than quantitative purposes, useful information regarding, for example, blockages in one or more vessels and/or whether blockages are resulting in the prevention of blood flow to related tissue may be obtained. Further, some quantitative information, for example, cardiac output determined from a slope of an intensity curve of the sample projections, may be obtained and utilized in various embodiments.

With continued reference to FIG. 1, the determination module 124 may be communicably coupled to the control module 126, with the control module 126 configured to control the CT acquisition unit 110 and/or other aspects of the system 100 to collect the reference and sample projections (and, in some embodiments, candidate projections), and to perform the imaging scans called for by the determination module 124. For example, the X-ray source 112 may be activated for relatively short lengths of time to acquire the various sample or candidate projections, and for relatively longer lengths of time (e.g., one full rotation) to acquire one or more imaging scans.

The output unit 140 is configured to provide information to the user. The output unit 140 may be configured to display, for example, an intensity curve, or, as another example, one or more images using information obtained during one or more corresponding imaging scans (e.g., an arterial phase image and a venous phase image). The output unit 140 may include one or more of a screen, a touchscreen, a printer, or the like.

The input unit 150 may be configured to obtain an input that corresponds to one or more settings or characteristics of a scan to be performed, and to provide the input (or information corresponding to the input) to the processing unit 120, which may use the input to determine, adjust, or select the position of one or more reference projections, the number and position of views for candidate projections, a rotational speed of a gantry, the number and type of imaging scans to be performed, the relationship to be used to determine the time for triggering imaging scans based on intensities, the region of interest or portion thereof for which intensities are to be determined, the threshold or criteria used to determine timing of imaging scanning triggering, or the like. The input may include, for example, a portion of the body to be scanned (e.g., head, body). The input unit 150 may be configured to accept a manual user input, such as via a touchscreen, keyboard, mouse, or the like. Additionally or alternatively, the input unit 150 may receive information from another aspect of the imaging system 100, another system, or a remote computer, for example, via a port or other connectivity device. The input unit 150 may also be configured to obtain user approval or denial of a proposed scanning setting.

Figure 6:
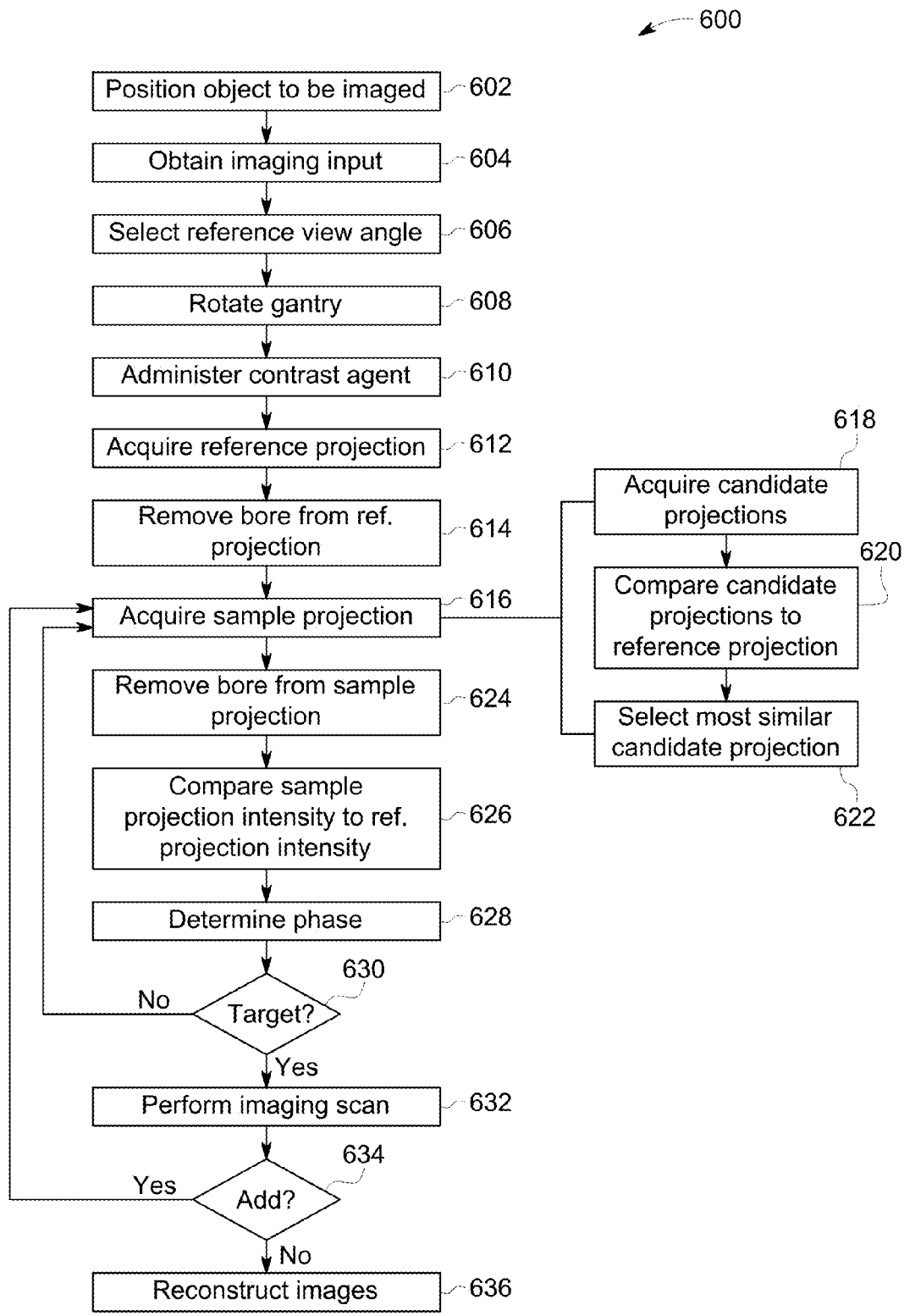
FIG. 6 is a flowchart of a method in accordance with various embodiments.

FIG. 6 provides a flowchart of a method 600 for imaging an object, for example as part of a perfusion study, in accordance with various embodiments. The method 600, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 600 may be able to be used as one or more algorithms to direct hardware (e.g., one or more aspects of the processing unit 120) to perform one or more operations described herein.

At 602, an object to be imaged is positioned. For example, the object may be a human patient positioned on a table in a bore of a CT imaging system. At 604, imaging input is obtained. For example, the imaging input may include a user input that includes scanning operational parameters (e.g., tube voltage, tube current, or the like) or information from which such parameters may be determined. The input may also include an identification of a body portion (e.g., head, body), and/or information describing or corresponding to a scan protocol or diagnostic purpose for a resulting image. The input may be utilized for example, to set scanning parameters, as well as to select positions or view angles for reference projections and candidate projections, as well as phases or portions thereof for which imaging scans will be performed.

At 606, a reference view angle is selected. For example, an anterior or posterior view may be selected as a view angle for which to obtain a reference projection for a perfusion study of a torso or portion thereof. As another example, a lateral side view may be selected as a view angle for which to obtain a reference projection for a perfusion study of a head or portion thereof. It may be noted that more than one reference projection may be acquired in various embodiments (e.g., a reference projection may be acquired from both a posterior and an anterior view angle or azimuth).

At 608, a gantry of a CT acquisition system is rotated, and, at 610, a contrast agent is administered to an object to be imaged. For example, a patient may be injected with a contrast agent proximate a region of interest for which a perfusion study is to be performed. At 612, a reference projection (or projections) is acquired at the reference view angle (or angles) selected at 606. It may be noted that the reference projection may be acquired, for example, shortly before the injection of contrast agent, shortly after injection (e.g., before a noticeable or significant amount of uptake of the contrast agent has occurred or at same time). The reference projection may be acquired during a first rotation of the CT acquisition system. At 614, in the illustrated embodiment, bone and/or other high density materials or structures (e.g., metallic implants) may be removed from the reference projection.

At 616, with the CT acquisition system still rotating, a sample projection is acquired. For example, in some embodiments, one sample projection may be acquired per rotation. The sample projection may be acquired at or near the same view angle that was used for the reference projection. In some embodiments, the sample projection may be acquired using a series of substeps, such as substeps 618, 620, and 622.

For example, at 618, candidate projections are acquired. The candidate projections may be acquired at or near the view angle for the reference projection. In some embodiments, the candidate projections may be spaced apart, while in other embodiments, one or more candidate projections may be consecutive or immediately adjacent each other. At 620, the candidate projections are compared to the reference projection. In some embodiments, the candidate projections may be compared to the reference projection before bone or other high density structures are removed from the candidate projections and reference projection. At 622, the candidate projection most similar to the reference projection is selected as the sample projection for a given rotation (e.g., the projection for which an intensity will be compared to an intensity of the reference projection).

In the depicted embodiment, at 624, bone and/or other high density materials or structures are removed from the sample projection. Then, at 626, the intensity for the sample projection (e.g., with bone information removed) is compared to the intensity for the reference projection (e.g., with bone information removed). In some embodiments, a difference between the sample projection and reference projection may be taken to provide a difference projection that corresponds to or represents the contrast agent distribution in the region of interest. In alternate embodiments, the intensities for the reference and sample projections may be determined separately (e.g., a sum of total intensity for each projection may be computed) and subsequently compared. It may be noted that in some embodiments, the intensities may be compared for an entire region of interest or organ of interest, while in other embodiments, intensities for a particular vascular structure or structures, instead of an entire organ, may be compared.

At 628, the current (e.g., at the time of acquisition of the sample projection) stage or phase of perfusion is determined, based on the comparison of intensities of the reference and sample projection. In some embodiments, the determination of the stage or phase of perfusion may be a determination of whether or not a particular stage or phase for triggering an imaging scan has been reached. The determination of whether or not to trigger or implement an imaging scan may be based on if a threshold slope and/or other intensity measure has been reached. The particular threshold may be experimentally determined, and may vary based, for example, on a slope of an intensity curve fitted to information provided by comparing a series of sample projections to the reference projection, as discussed herein.

At 630, if it is determined at 628 that a target stage or phase has been reached, an imaging scan may be performed at 632. If the target stage or phase has not been reached, the method may proceed back to 616 to acquire a next sample projection (e.g., from next rotation).

At 632, a scan is performed. The X-ray source and detector may be rotated about the object being imaged and operated in a manner prescribed by predetermined scanning parameters to collect imaging information at the detector. Imaging or projection data or information is obtained via the detector during the performance of the scan. For example, the scan may be performed for arterial phase imaging at or near a peak normalized intensity value. As another example, the scan may be performed for venous phase imaging at or near a local minimum normalized intensity value.

At 634, it is determined if an additional image is desired (e.g., an image for another perfusion phase, or an image for a later portion of a given perfusion phase) is desired. If another image is desired, the method 600 may proceed to 616. If no further images are desired, the method 600 may proceed to 636. At 636, one or more images are reconstructed (e.g., using reconstruction module 122 or other aspect of processing unit 120). An image may be reconstructed for each imaging scan performed.

It may be noted that while the above examples relate generally to perfusion studies, that various embodiments may be utilized in connection with additional diagnostic modes, techniques, or purposes. For example, various embodiments may be utilized in conjunction with general diagnostic studies, or, as another example, in conjunction with run-off studies. In a run-off study, a flow rate may be determined or obtained and used to adjust the velocity of a helical scan.

In various embodiments, not only the arrival of contrast agent in a particular region or regions may be monitored, but also a directionality or other characteristic of movement, flow, or distribution of the contrast agent may be determined. In some embodiments, a CT system having wide collimation may be utilized. Wide collimation, as used herein, may be understood as collimation along a length (or z-axis, or axis normal to a plane of rotation of a CT gantry) of an object being imaged sufficiently sized to provide an image or imaging information covering one or more regions viewed along the length of the object. In contrast, conventional narrow collimation provides a view directed axially through the object, or of a single slice taken through an object. By way of example, some embodiments provide for a 160 millimeter collimation along a z-axis or length of an object being imaged. Generally, in some embodiments, a collimation greater than 5 millimeters may provide a wide collimation as used herein. As examples, a wide collimation in various embodiments may provide a collimation along a length of an object of 10 millimeters, 20 millimeters, 50 millimeters, 100 millimeters, 150 millimeters, or more.

In various embodiments, visualization of contrast flow along a direction (or directions) of flow and/or estimation of speed of contrast flow may be provided during all or a portion of contrast enhanced scanning. For example, flow rate information (e.g., speed) may be utilized to modify scanning parameters to image anatomy at an appropriate time and/or speed. Additionally or alternatively, the timing for acquisition of a volume of CT scans may be optimized.

Certain conventional approaches for detecting arrival of contrast agent rely upon use of axial scans to detect contrast enhancement in a vessel (or artery) upstream of a diagnostic region of interest. However, such conventional images are viewed in an axial plane, but contrast agent generally flows into and out of the axial plane being viewed. As a result, the utility of such images to measure the flow rate of contrast agent is inherently limited. Various embodiments described herein provide improved visualization, estimation, and/or determination of flow rate by providing imaging information taken along a longitudinal view (in contrast to axial views) of an object.

Figure 7:
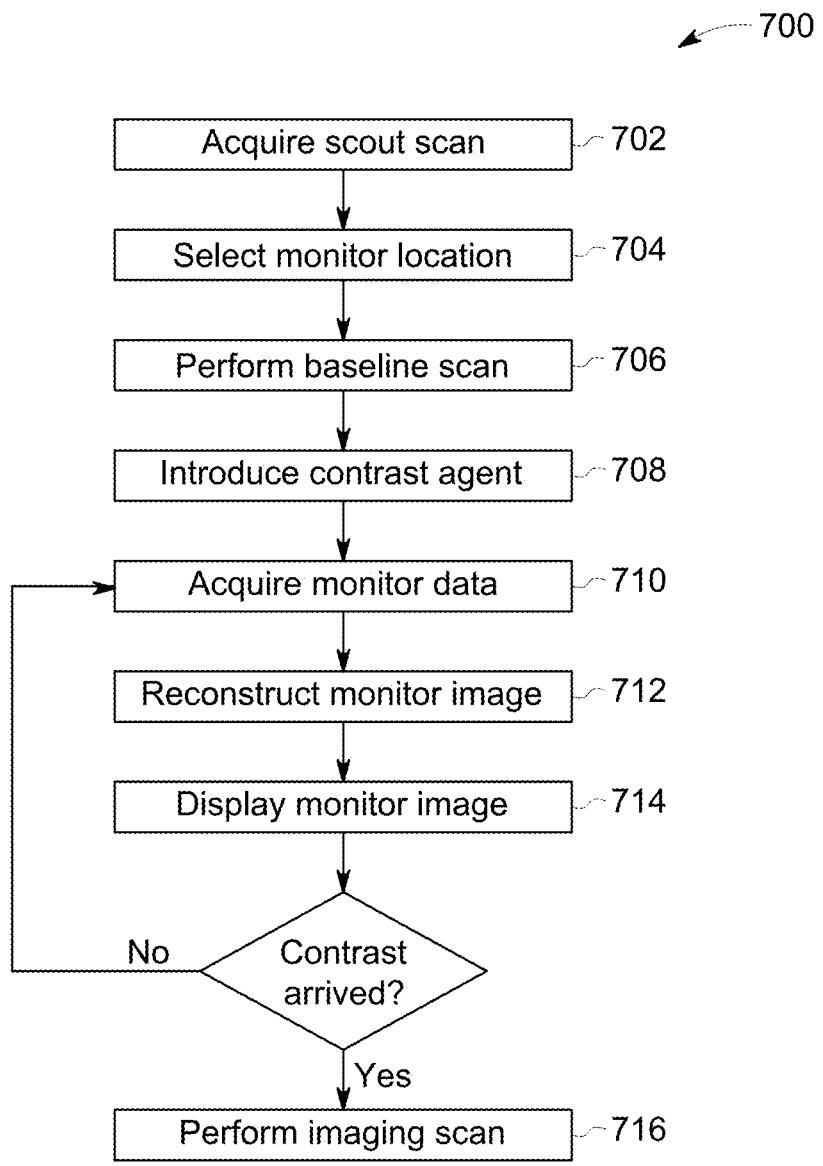
FIG. 7 is a flowchart of a method in accordance with various embodiments.

FIG. 7 provides a flowchart of a method 700 for imaging an object, for example for use of sample projections to determine a time (or times) to perform an imaging scan, in accordance with various embodiments. The method 700, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. It may be noted that aspects of the method 600 may be performed in conjunction with or as part of the method 700. In various embodiments, portions, aspects, and/or variations of the method 700 may be able to be used as one or more algorithms to direct hardware (e.g., one or more aspects of the processing unit 120) to perform one or more operations described herein.

At 702, a scout scan is acquired. The scout scan may be acquired to plan scanning of a patient. For example, a scout scan may be utilized to identify the location of organs and/or regions of interest of the patient, for example to determine how much of the patient is to be scanned for a particular clinical or diagnostic task. A gantry may be stationary during acquisition of the scout scan.

At 704, a monitor location (or target region) is selected. The monitor location is a location of the patient that will be monitored to track the progress (e.g., beginning, peak, end, development, distribution) of contrast enhancement. The monitor location may be selected based on anatomical information determined from the scout scan as well as based on the particular clinical or diagnostic task of the scanning procedure. In various embodiments, the monitor location may cover a range or ranges viewed along a length of the patient. For example, the monitor location may include an organ or region of interest, as well as a region (or regions) upstream or downstream of the region of interest relative to the flow of contrast agent.

At 706, a baseline scan is performed. In the illustrated embodiment, the baseline scan is performed before injection of a contrast agent. The baseline scan may be performed at one or more monitor locations or target regions selected or identified at 704. The baseline scan may be understood as a reference projection as used herein, and may be used to provide a reference to which subsequent projections may be compared to determine contrast enhancement. The baseline scan may be acquired at one or more reference or projection views as discussed herein (see. e.g., steps 608-614 of method 600). At 708, contrast agent is introduced into the patient.

At 710, monitor data is acquired. The monitor data may include one or more projections (e.g., sample projections) taken for the location selected at 704. Sample projections may be taken over time to track the progress, directionality, and/or distribution of contrast enhancement for a region of interest. When the contrast enhancement satisfies a particular criteria, a full imaging scan (e.g., acquiring imaging data over a full rotation of view angles) may be performed.

Figure 8:
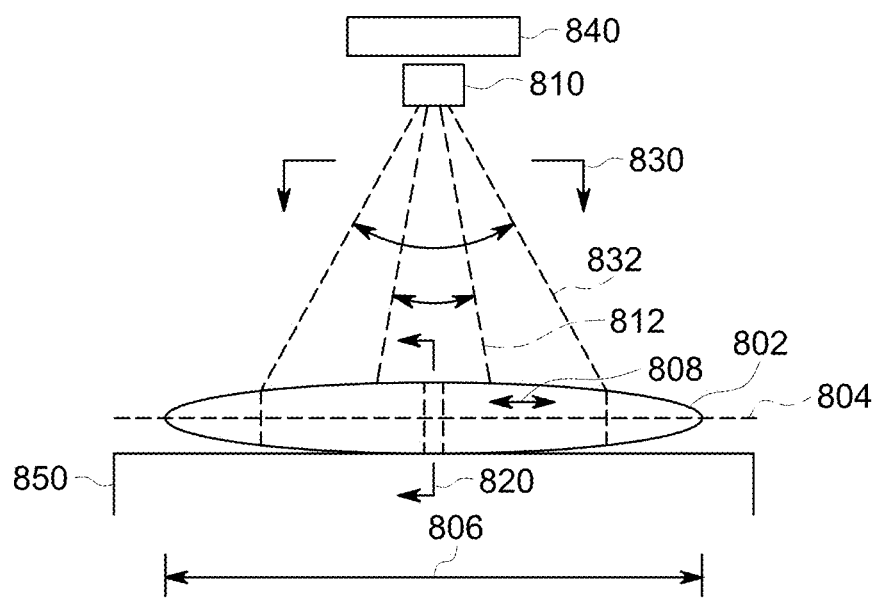
FIG. 8 provides a schematic view of a wide angle collimation utilized in accordance with various embodiments.

It may be noted that the baseline scan or reference projection, as well as the monitor data or sample projection(s) may be acquired using a wide collimation as discussed herein. FIG. 8 provides a schematic view of an imaging system 800 that utilizes wide collimation in accordance with various embodiments. As seen in FIG. 8, the imaging system 800 includes an X-ray source 840, a wide collimator 810, and a bed 850. The X-ray source 840 and wide collimator 810 are configured to rotate about the bed 850 (e.g., using a rotating gantry). An object 802 (e.g., a patient) having a longitudinal axis 804 is supported by the bed 850 during imaging. X-rays from the X-ray source 840 pass through the object 802 and are attenuated, with the attenuated X-rays received by a detector (not shown in FIG. 8) and used to reconstruct an image. As seen in FIG. 8, the object 802 has a length 806 extending along the longitudinal axis 804. Contrast agent flows in a direction of flow 808 that is generally parallel to the longitudinal axis 804 in the illustrated embodiment.

Conventional or narrow collimation provides a relatively narrow collimation field of view 812 as shown in FIG. 8. For example, the narrow collimation field of view 812 may have a width of 5 millimeters or less through the object 802, and may be used to reconstruct an axial slice or view in an axial plane. Such an axial slice or view may be understood as being viewed in direction 820 as shown in FIG. 8. However, the wide collimator 810 provides a wide collimation field of view 832 as seen in FIG. 8. The wide collimation field of view 832 may be greater than 5 millimeters. For example, in the illustrated embodiment, the wide collimation field of view has a width of 160 millimeters along the longitudinal axis 804 at the center of the object 802. The wide collimation field of view 832 may be used to provide a longitudinal view, or view taken along direction 830 as seen in FIG. 8 (e.g., a view along the length of the object 802, or at about 90 degrees to the view angle for an axial slice).

Figure 9A:
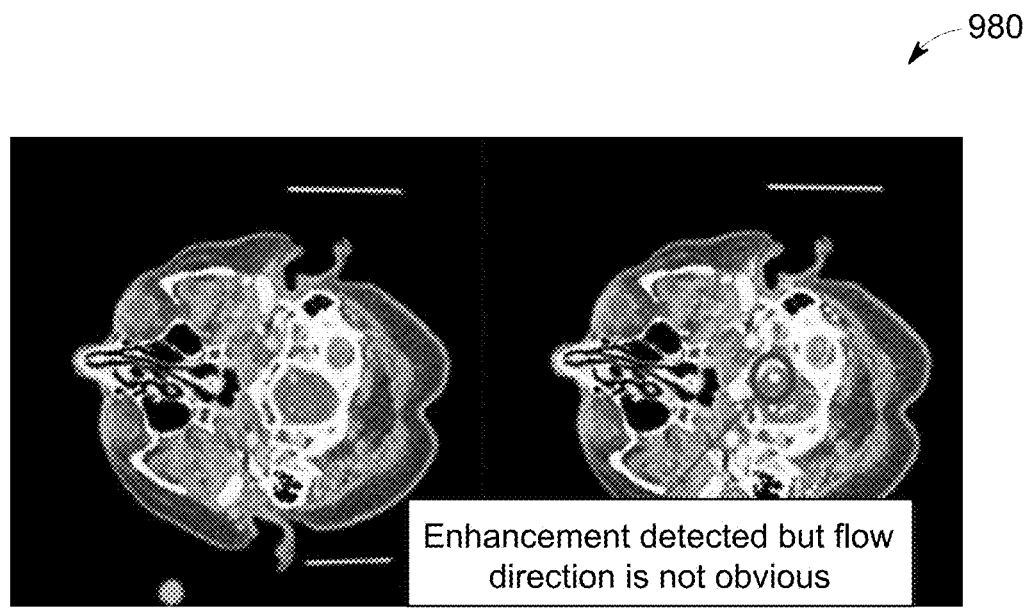
FIGS. 9A-E illustrate longitudinal and axial views of contrast enhancement in accordance with various embodiments.
Figure 9B:
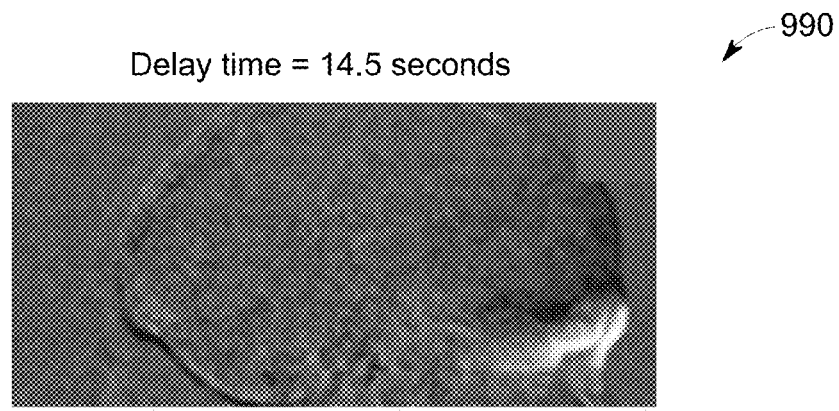
Figure 9C:
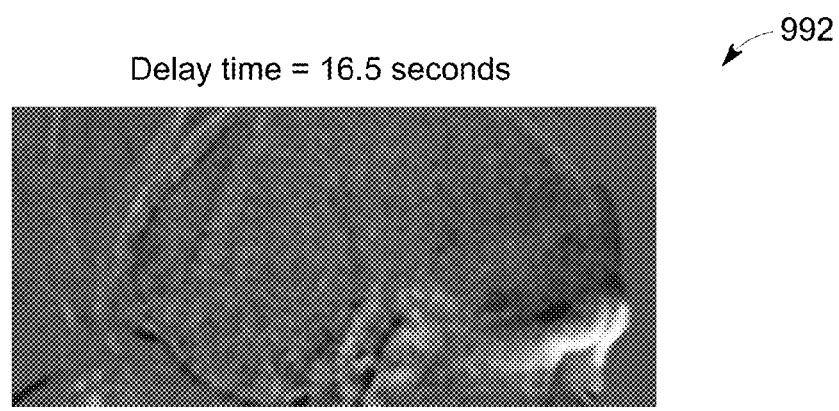
Figure 9D:
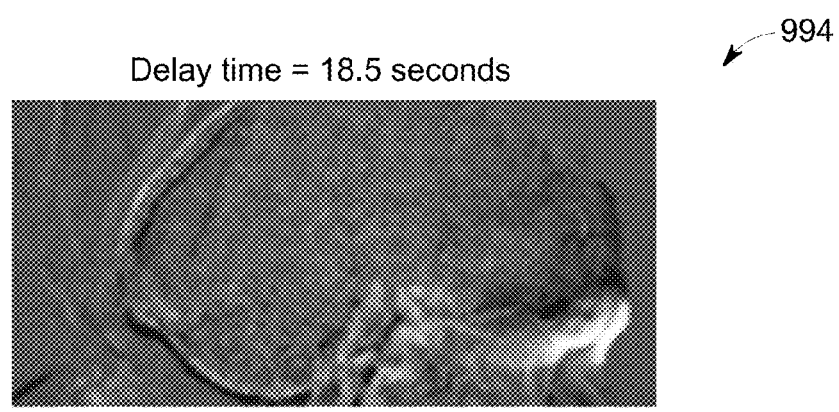
Figure 9E:
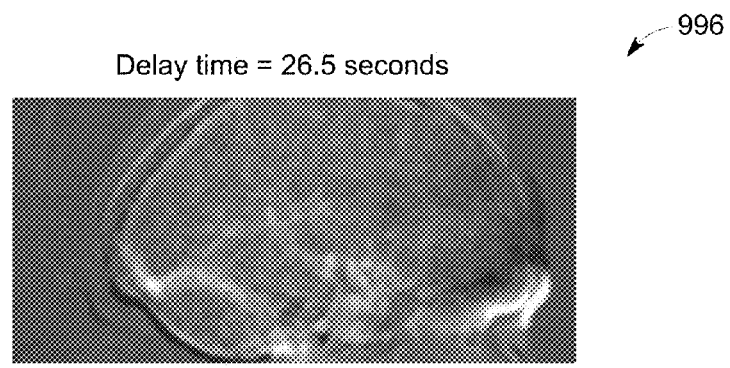

Use of a longitudinal view as provided by the wide collimator 810 in various embodiments provides for viewing or visualization of directionality and/or distribution of contrast enhancement or contrast agent flow. For example, FIG. 9A illustrates an axial view 980 (e.g., a view taken along 820 acquired using the narrow collimation field of view 812). Because the axial view 980 is viewed orthogonal to the direction of flow 808, enhancement or the arrival of contrast agent may be detected using images viewed with the axial view 980 at different times, but flow direction is not obvious, nor may flow distribution be viewed. Further, using the axial view 980, enhancement may only be detected at one axial location. However, by using a longitudinal view as provided by various embodiments disclosed herein (e.g., a view along 830 provided by the wide collimator 810), flow direction and distribution may be viewed, and the presence (or absence) of enhancement at various locations along the axis or length of the object 802 may be detected or determined.

For example, FIGS. 9B-9E illustrate views 990, 992, 994, 996, respectively, taken along a length (or portion thereof) of the object 802 at different times. For example, the axial view 980 may provide a cross-section of an anatomical structure (e.g., skull) at one axial location, while the views 990, 992, 994, 996 may provide a profile or other view of a side, front, or rear of a skull (depending on the view angle of a given projection). As seen in FIGS. 9B-9E, the contrast enhancement (shown by relatively lighter areas) may be tracked and monitored over time. Based on the contrast enhancement at one or more locations, one or more imaging scans may be triggered or performed at advantageous times to take advantage of the contrast enhancement. It may be noted that the views 990, 992, 994, 996 may be obtained using one or a few sample views per rotation instead of a full rotation, with the sample view(s) or projection(s) compared to a reference or baseline projection as discussed herein to determine contrast enhancement (e.g., steps 618-626). It may be noted that the comparison of reference projections taken at different times using a wide collimation (e.g., as seen in views 990, 992, 994, 996) may provide distributional and/or directional information of flow of a contrast agent.

For example, for the embodiment illustrated in FIG. 9B-E, a CT perfusion dataset may be acquired with an inter scan delay of 2 seconds. One projection from each acquisition at a fixed tube angle (e.g., 90 degrees) may be used to generate a monitor image. In some embodiments, the monitor image may be generated using projection data after applying reference normalization, air correction, and/or negative logarithm operations that are typically performed as part of pre-processing during CT reconstruction. The projection data from the first, reference, or baseline acquisition may then be subtracted from each subsequent acquisition to determine the cumulative change in contrast with respect to the start of the injection. It may be noted that the particular example implementation discussed herein is meant by way of example, and that alternate or additional techniques may be employed in various embodiments. Generally, a spatiotemporal filter may be employed to visualize contrast flow. It may further be noted that variations in the scan technique and/or the technique employed to generate monitor data to visualize contrast flow may be employed. For example, variations in scan technique include use of a scan type where a scanogram may be acquired to visualize the contrast in either coronal or sagittal image plane over time to estimate the arrival of contrast. Further, in various embodiments, wide collimation axial images (additionally or alternatively to wide collimation longitudinal images as discussed herein) may be acquired, however acquisition of wide collimation axial images may result in a significantly higher radiation dose.

Returning to FIG. 7, at 712, a monitor image is generated using the monitor data acquired at 710. For example, the monitor image may be generated using one or more pre-processing steps, such as reference normalization, air correction, and or negative logarithmic operation. In some embodiments, where multiple projection views are acquired, a monitor image may be generated using tomosynthesis in addition to one or more other pre-processing steps, with the tomosynthesis image providing depth information to further enhance the contrast uptake. As discussed herein, the monitor image or sample projection may include sufficient information to determine contrast enhancement, but not sufficient information for reconstruction of an imaging scan image. At 714, the monitor image may be presented, for example, for viewing by an operator.

At 714, it is determined if the contrast agent has arrived (e.g., if a sufficient amount of the contrast agent has arrived or a desired distribution of contrast agent has arrived). In some embodiments, the determination of whether the contrast agent has arrived may be made by an operator viewing displayed monitor images, while in other embodiments, the determination may be made automatically. If the contrast agent, or a desired amount of contrast agent, level of contrast enhancement, and/or distribution of contrast agent has not arrived, the method 700 may return to 710 and acquisition of subsequent monitoring data may be performed. If, however, the contrast agent, or a desired amount of contrast agent, level of contrast enhancement, and/or distribution of contrast agent has arrived, the method 700 may proceed to 716, and a diagnostic scan or imaging scan may be performed. By tracking or monitoring the contrast enhancement using relatively low dose projections (e.g., acquired at one or a few views instead of over a full rotation), a preferred time for performing a full, diagnostic, or imaging scan may be selected to take full or increased advantage of the contrast agent, while lowering overall dose for a scanning procedure. The monitor images taken at different times thus may be used to select a time for performing one or more full diagnostic scans, and/or to determine a rate and/or distribution of contrast agent over time.

It may be noted that, in some embodiments, monitor images or projections may be acquired from different view angles and displayed or otherwise used to evaluate the flow of contrast in 3D. For example, when monitor images are displayed from 0 degrees and 90 degrees, it is possible to determine the contrast flow along x-, y-, and z-axes. Advanced techniques may be employed to visualize contrast flow in three dimensions. For example, enhancement information may be overlayed on a 3D image volume acquired before acquisition of the monitor images or sample projections.

Further, in various embodiments, contrast flow may be estimated or determined, for example, using enhancement curves at two or more different locations of an object (e.g., human patient) generated using monitoring images or sample projections at the two or more different locations. The estimation of contrast flow rate may be made along a vessel length and/or along a table length (e.g., z-axis), for example using monitoring images or sample projections acquired at different times for two or more locations using wide collimation longitudinal views as discussed herein.

Figure 10A:
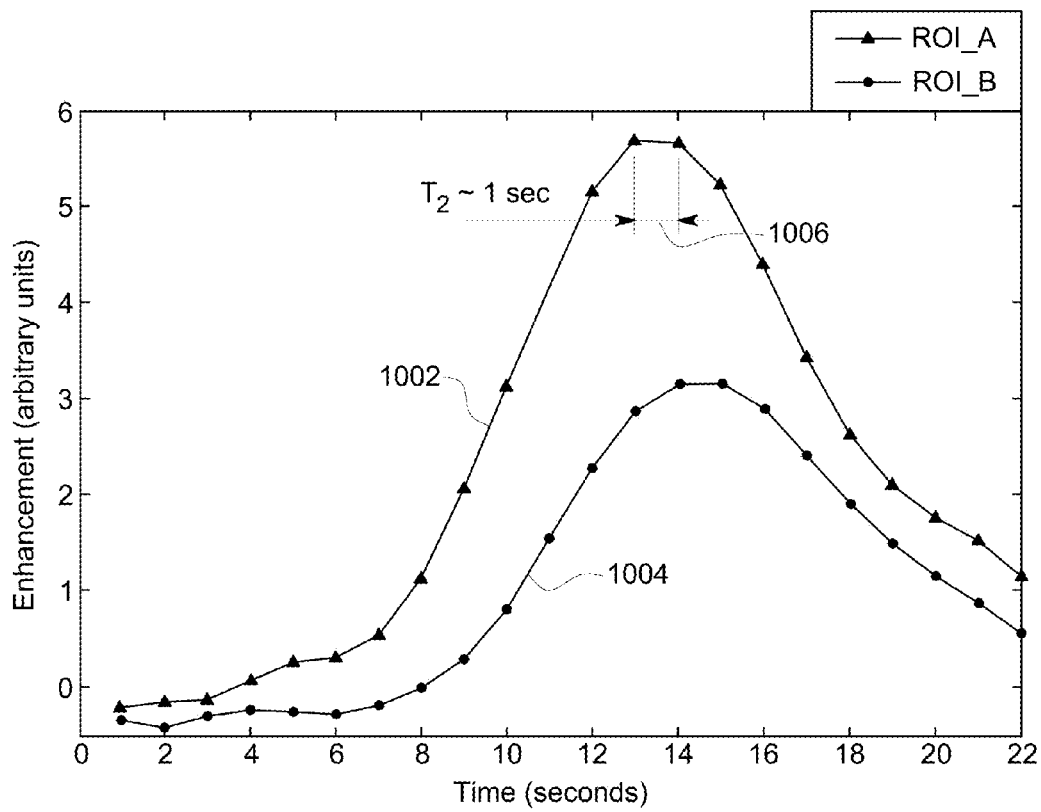
FIGS. 10A-F provide various graphs illustrating flow rate estimation in accordance with various embodiments.

FIG. 10A illustrates various examples of enhancement curves that may be utilized to determine contrast flow rate information. For example, in FIG. 10A, a first enhancement curve 1002 for a first location and a second enhancement curve 1004 for a second location are plotted over time against a vertical axis of amount of contrast enhancement. The depicted example is provided for illustrative purposes, and no particular unit of contrast enhancement is specified for the example. As seen in FIG. 10A, the time 1006 between the peaks of the first enhancement curve 1002 and the second enhancement curve 1004 is about 1 second. Thus, the time required for contrast to flow from the first location to the second location may be estimated as about 1 second. Alternate techniques may be employed in various embodiments.

Figure 10B:
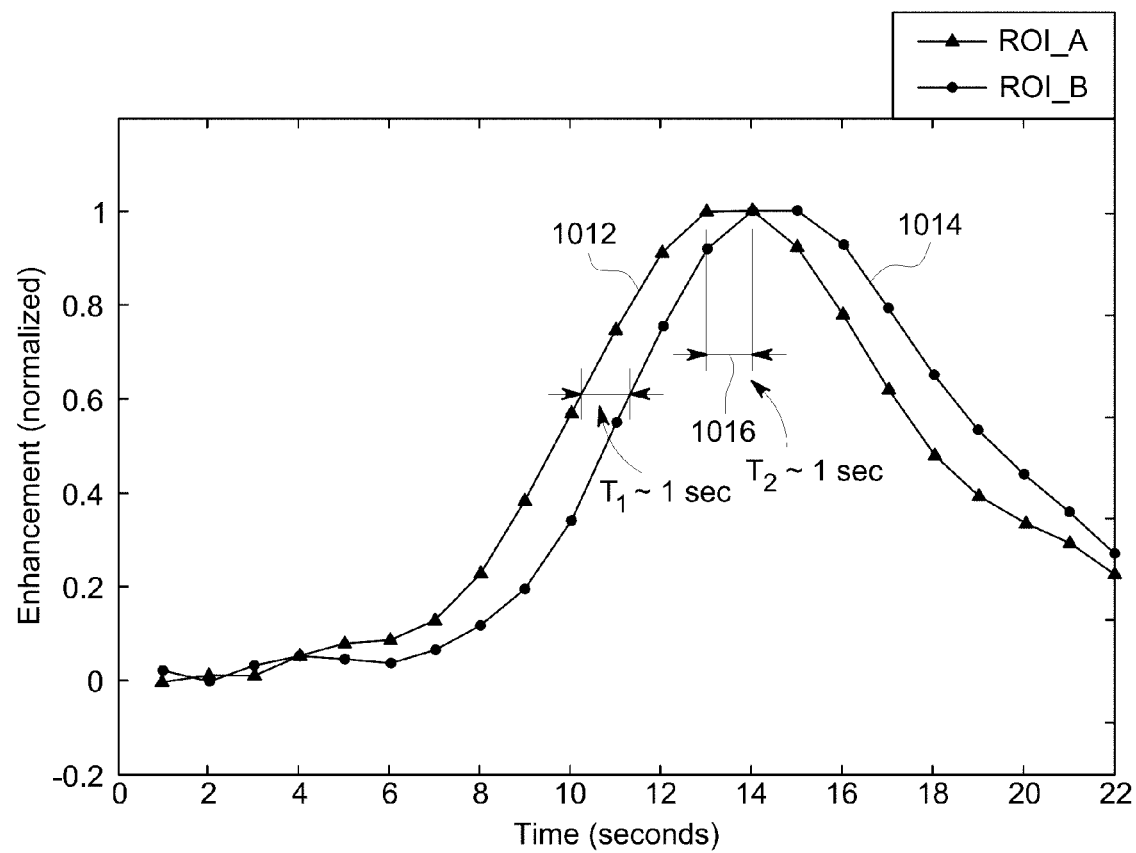

For example, FIG. 10B illustrates the use of normalization with enhancement curves. FIG. 10B is similar to FIG. 10A in certain respects, but is plotted against a normalized vertical axis (e.g., maximum contrast enhancement at 1.0). As seen in FIG. 10B, a first enhancement curve 1012 for a first location and a second an enhancement curve 1014 for a second location are plotted over time against a vertical axis of amount of contrast enhancement. As seen in FIG. 10B, the time 1016 between the peaks of the first enhancement curve 1012 and the second enhancement curve 1014 is about 1 second. Thus, the time required for contrast to flow from the first location to the second location may be estimated as about 1 second.

Generally, flow rate may be estimated based on enhancement curves measured at two different location by using either a difference in time to reach a given threshold, or a difference in time to reach a peak, for example. If the amount of enhancement at the two locations is different, the difference in time to peak may be used. If the amount of enhancement at two locations is different, normalized enhancement curves may be used with a normalized threshold for estimating the time needed for contrast to flow from the first location to the second location.

Figure 10C:
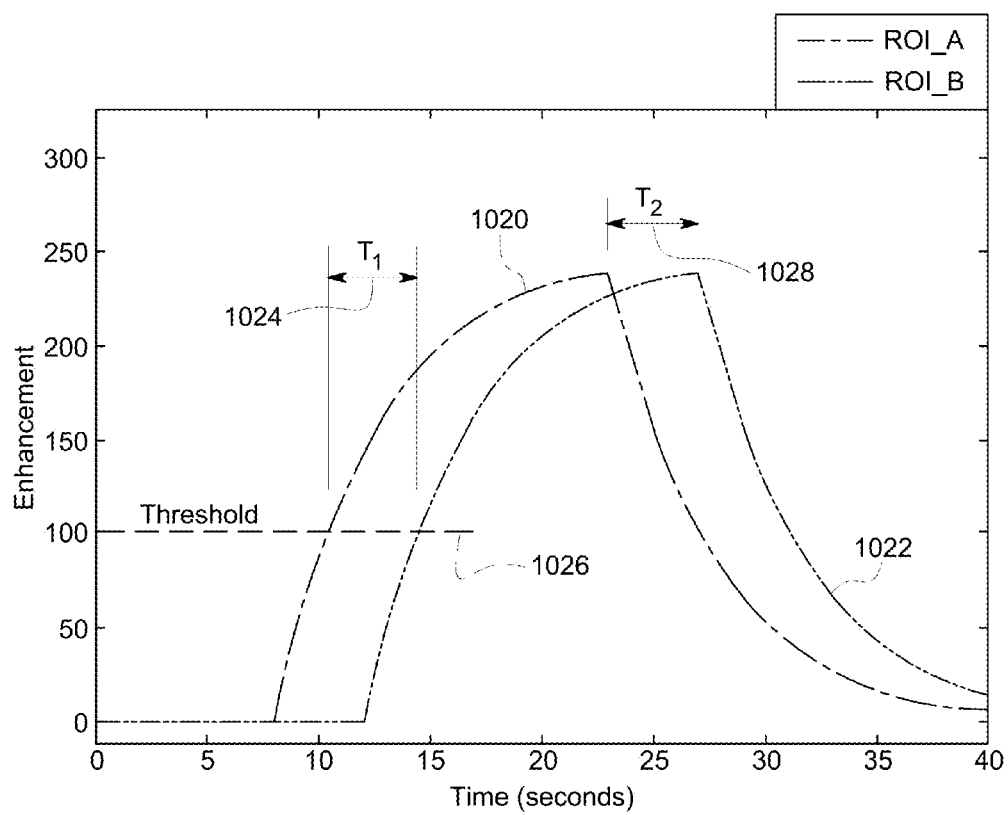

FIG. 10C provides an example of the use of a difference in time to reach a threshold as well as a difference in time to reach a peak. In FIG. 10C, a first enhancement curve 1020 for a first location has a same peak enhancement intensity as a second enhancement curve 1022 for a second location. Further, the first enhancement curve 1020 and second enhancement curve 1022 have generally the same shape or profile. Accordingly, either a threshold time 1024 (e.g., a time between the time of the first enhancement curve 1020 crossing a threshold 1026 and the time of the second enhancement curve 1022 crossing the threshold 1026) may be employed to estimate flow rate, or a peak time 1028 (e.g., a time between the time of the first enhancement curve 1020 peaking and the time of the second enhancement curve 1022 peaking) may be employed to estimate flow rate. In various embodiments, a threshold time and peak time may be combined (e.g., averaged or otherwise combined) to determine or estimate flow rate.

Figure 10D:
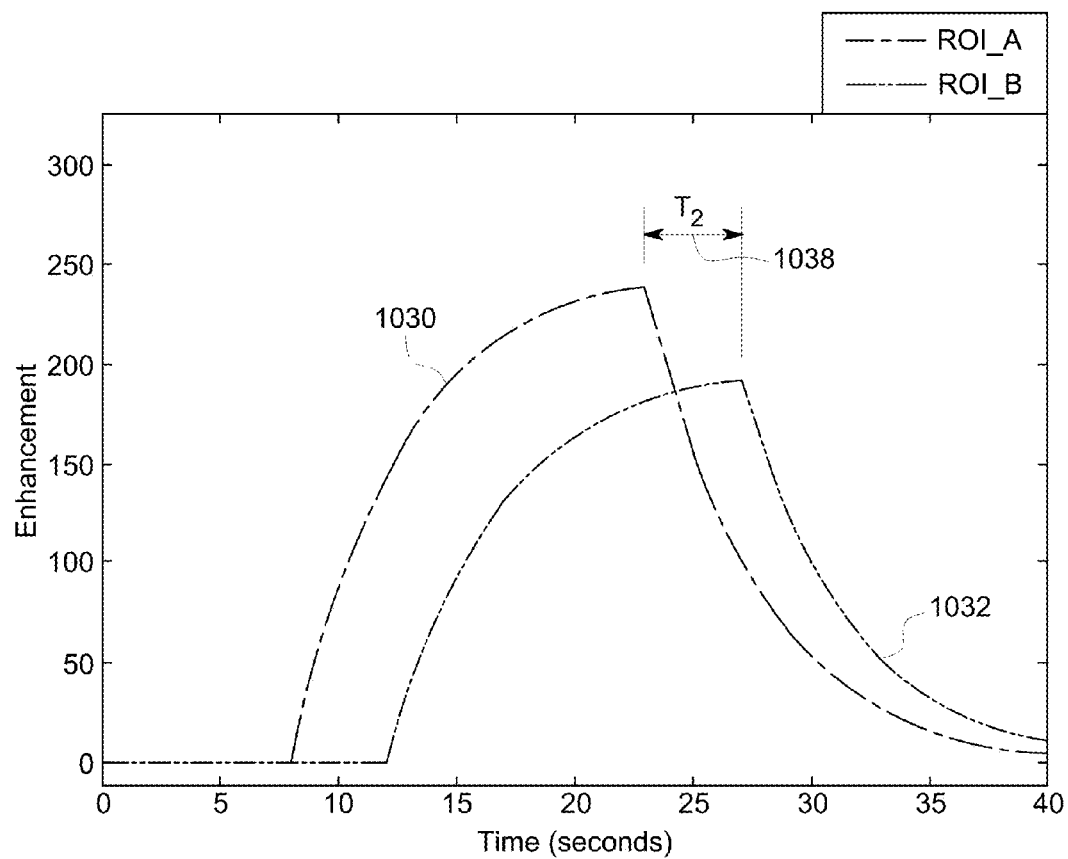

FIG. 10D provides an example of the use of a difference in time to reach a peak. In FIG. 10D, a first enhancement curve 1030 for a first location has a different peak enhancement intensity than a second enhancement curve 1032 for a second location, and the two enhancement curves have generally different slopes or profiles approaching their respective peaks. Accordingly, reaching a given threshold of a given unit of enhancement may not provide an accurate comparison of the two locations. In FIG. 10D, a peak time 1038 (e.g., a time between the time of the first enhancement curve 1030 peaking and the time of the second enhancement curve 1032 peaking) may be employed to estimate flow rate.

Figure 10E:
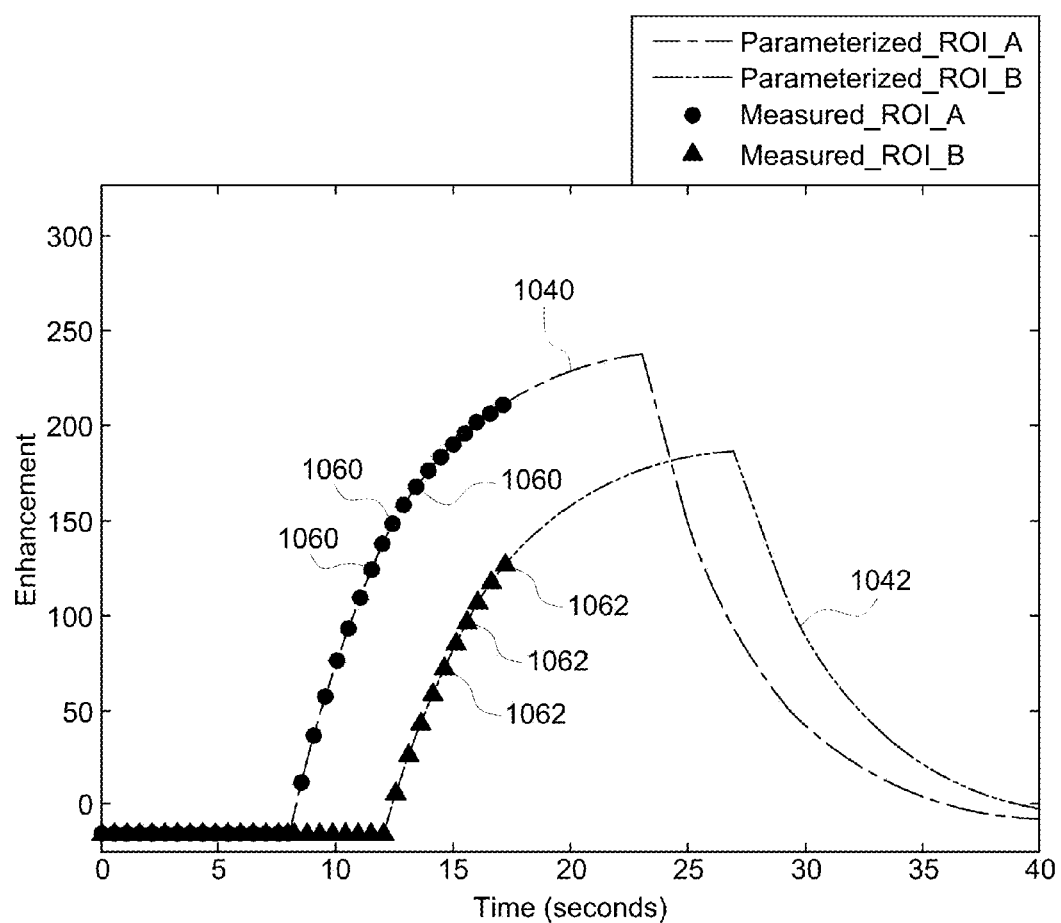
Figure 10F:
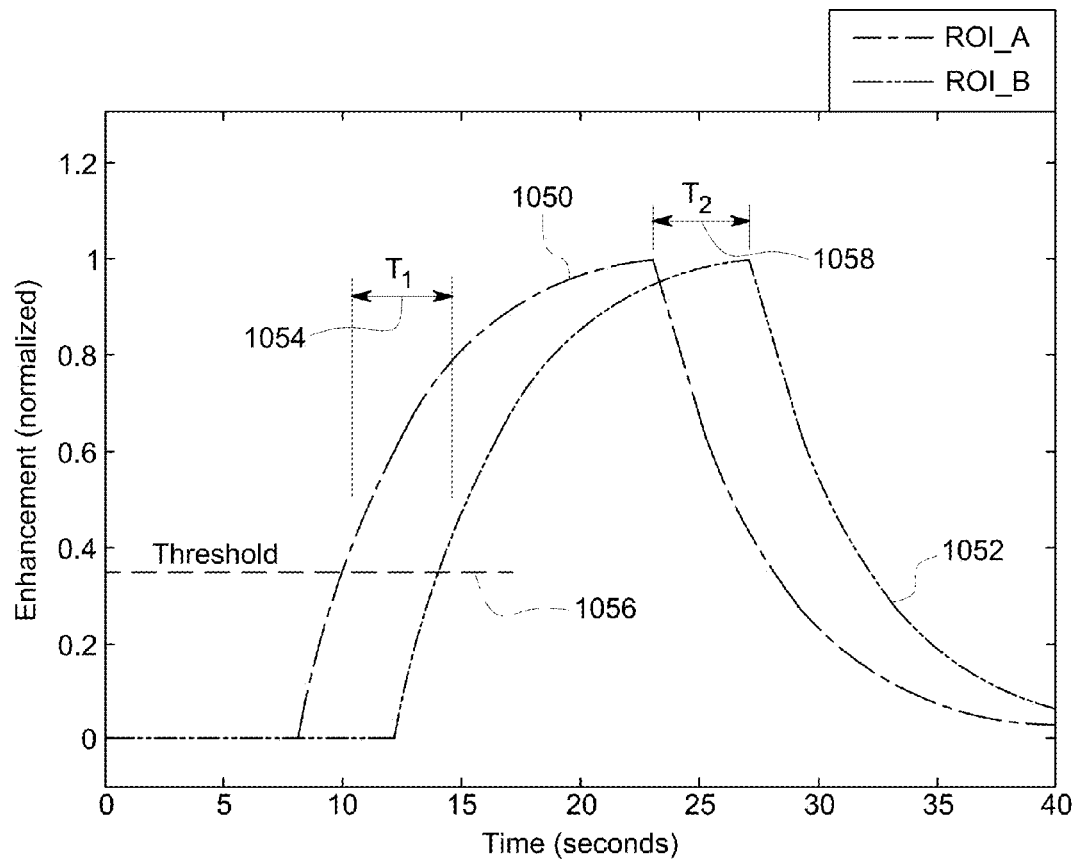

FIGS. 10E and 10F provide an example of enhancement curves having different peaks and/or shapes that are normalized to allow comparison of a threshold as well as a peak. As seen in FIG. 10E, a first enhancement curve 1040 for a first location has a different peak enhancement intensity than a second enhancement curve 1042 for a second location, and the two enhancement curves have generally different slopes or profiles approaching their respective peaks. However, the differently shaped and peaked measured curves of FIG. 10E may be normalized to similarly shaped normalized curves shown in FIG. 10F having similar peaks (e.g., at a normalized value of 1.0). As seen in FIG. 10F, a first normalized enhancement curve 1050 (e.g., a normalized curve of first enhancement curve 1040) for a first location has a same peak enhancement intensity as a second normalized enhancement curve 1052 (e.g., a normalized curve of the second enhancement curve 1042) for the second location. As seen in FIG. 10F, the first normalized enhancement curve 1050 and the second normalized enhancement curve 1052 have generally the same shape or profile. Accordingly, either a threshold time 1054 (e.g., a time between the time of the first normalized enhancement curve 1050 crossing a normalized threshold 1056 and the time of the second normalized enhancement curve 1052 crossing the normalized threshold 1056) may be employed to estimate flow rate, or a peak time 1058 (e.g., a time between the time of the first normalized enhancement curve 1050 peaking and the time of the second normalized enhancement curve 1052 peaking) may be employed to estimate flow rate. Again, in various embodiments, a threshold time and peak time may be combined (e.g., averaged or otherwise combined) to determine or estimate flow rate.

Further, flow rate information (e.g., flow rate information determined using enhancement curves at two or more locations as discussed herein) may be utilized in various embodiments to optimize scanning parameters such as pitch, rotation time, and/or table speed. For example, for contrast enhanced scanning of extremities, a table speed may be selected to match a flow rate of contrast along the arteries. In certain conventional approaches, to achieve the table speed timing, bolus scans may be acquired at two different axial cross-sections, with the time for enhancement to peak for each location analyzed along with the distance between the two image planes. Various embodiments provide for improved contrast flow estimation as well as reduced dose and improved convenience. For example, longitudinal views in various embodiments allow for use of a single contrast injection instead of a series of bolus injections, as well as providing improved information for contrast presence or flow at additional locations compared to just two axial cross-sections.

Generally, during scanning, contrast information may be available at discrete individual times (represented by points 1060 and 1062 on FIG. 10E). However, the enhancement curves may be parameterized and used to estimate transport delay for estimating contrast flow rate. Once the flow rate is estimated, a table speed may be selected to match the flow rate. The contrast flow rate information may also be used to optimize the scan time. Further, once the table speed is known or determined, a combination of pitch, collimation, and rotation time may be selected to acquire each scan at an optimal or improved time. Such optimal or improved imaging times may help eliminate or reduce missed lesions and/or contamination of images with venous flows that may occur from imaging that occurs too early or too late.

In some embodiments, for contrast enhanced scanning with scan ranges over 160 millimeters, helical scans may be employed with table speed selected to image each plane when the contrast enhancement is at or near a peak when the particular plane is scanned. In certain conventional techniques, helical scans may be acquired at constant table speed that is estimated using two or more bolus scans at two different image planes separated by a known amount. However, such an estimate of contrast speed is a rough approximation (e.g., based on only two axial locations) and can lead to either imaging ahead of the time when contrast peaks at an image plane or after the contrast peaks at an image plane.

In contrast to conventional techniques, in various embodiments contrast flow rate may be estimated as the scanning is being performed (e.g., using longitudinal views and contrast enhancement curves). For example, projection data from one or more fixed view angles from each rotation may be used to monitor the contrast flow rate and update the table speed to help ensure that each image plane is acquired at or near peak contrast enhancement. It may be noted that with decreasing scan durations, and by taking advantage of faster table speeds and wider collimation, it may be possible to optimize the scanning parameters or technique based on measured contrast enhancement during the performing of the scanning process being optimized (e.g., without using separate bolus scans).

When axial scans are utilized for imaging different organs in the same scan, it is sometimes necessary to predict the arrival of contrast in each organ separately. In such scenarios, it may be possible to acquire axial images until the contrast arrives and then perform a diagnostic scan at each location when contrast enhancement peaks (or nears a peak) for each location. However, utilization of axial images for monitoring contrast may result in the cumulative dose the monitor scans quickly adding up. Further, there may be substantial risk of not detecting the contrast adequately due to monitoring of contrast flow in the axial direction (e.g., a direction orthogonal to the direction of flow), and/or because the magnitude of enhancement might not be adequate to detect the contrast arrival at each organ. In various embodiments, the use of longitudinal sample projections or monitor images may be employed, with monitor image generation being relatively fast (e.g., due to only information from one or a few view angles being utilized). With one or a few images acquired during the monitoring phase at each location before initiating diagnostic scans, overall dose may be reduced while acquiring diagnostic scans at appropriate times (e.g., at or near peak contrast enhancement).

Figure 11:
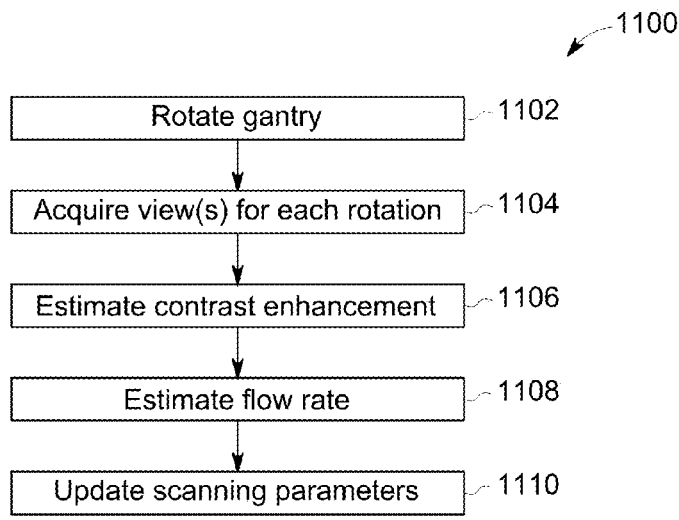
FIG. 11 is a flowchart of a method in accordance with various embodiments.

FIG. 11 provides a flowchart of a method 1100 for imaging an object, for example for use of sample projections to determine a time (or times) to perform an imaging scan, and/or to determine scanning parameters, in accordance with various embodiments. The method 1100, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. It may be noted that aspects of the methods 600 and/or 700 may be performed in conjunction with or as part of the method 1100. In various embodiments, portions, aspects, and/or variations of the method 1100 may be able to be used as one or more algorithms to direct hardware (e.g., one or more aspects of the processing unit 120) to perform one or more operations described herein.

At 1102, a gantry is rotated. For example, the gantry may begin rotation at or near a time of injection of contrast agent into a patient to be scanned, and continue rotation during the acquisition process.

At 1104, one view (or a few views) of imaging data may be acquired during each rotation. The sample projections or monitor images, for example, may be acquired using a wide collimation at a view angle at or near a view angle used to acquire a reference or baseline projection acquired before commencement of contrast enhancement at a region of interest.

At 1106, contrast enhancement is estimated. For example, as discussed herein, the contrast enhancement may be estimated by comparing information from one or more sample projections with a reference projection over time.

At 1108, flow rate is estimated. For example, as discussed herein, flow rate may be estimated using enhancement curves corresponding to enhancement at two or more locations. In various embodiments, a difference in time between enhancement peak and/or enhancement satisfying a threshold for two different locations may be used to estimate flow rate.

At 1110, scanning parameters are updated. In various embodiments, based on the contrast flow rate and/or the amount of enhancement, an optimal set of scan parameters may be determined. The scan parameters, or parameters used to guide the acquisition of scanning information, may include, for example, one or more of pitch, rotation time, table speed, inter-scan delay, or combination. As the computations used in conjunction with the sample projections or monitor images (e.g., projections taken at only one or a few view angles, instead of a full rotation or other amount corresponding to an imaging or diagnostic scan) are relatively non-intensive or have relatively low computational requirements, a computer intensive reconstruction technique may not be required and may be implemented in gantry firmware more readily than full diagnostic imaging reconstruction techniques.

Figure 12:
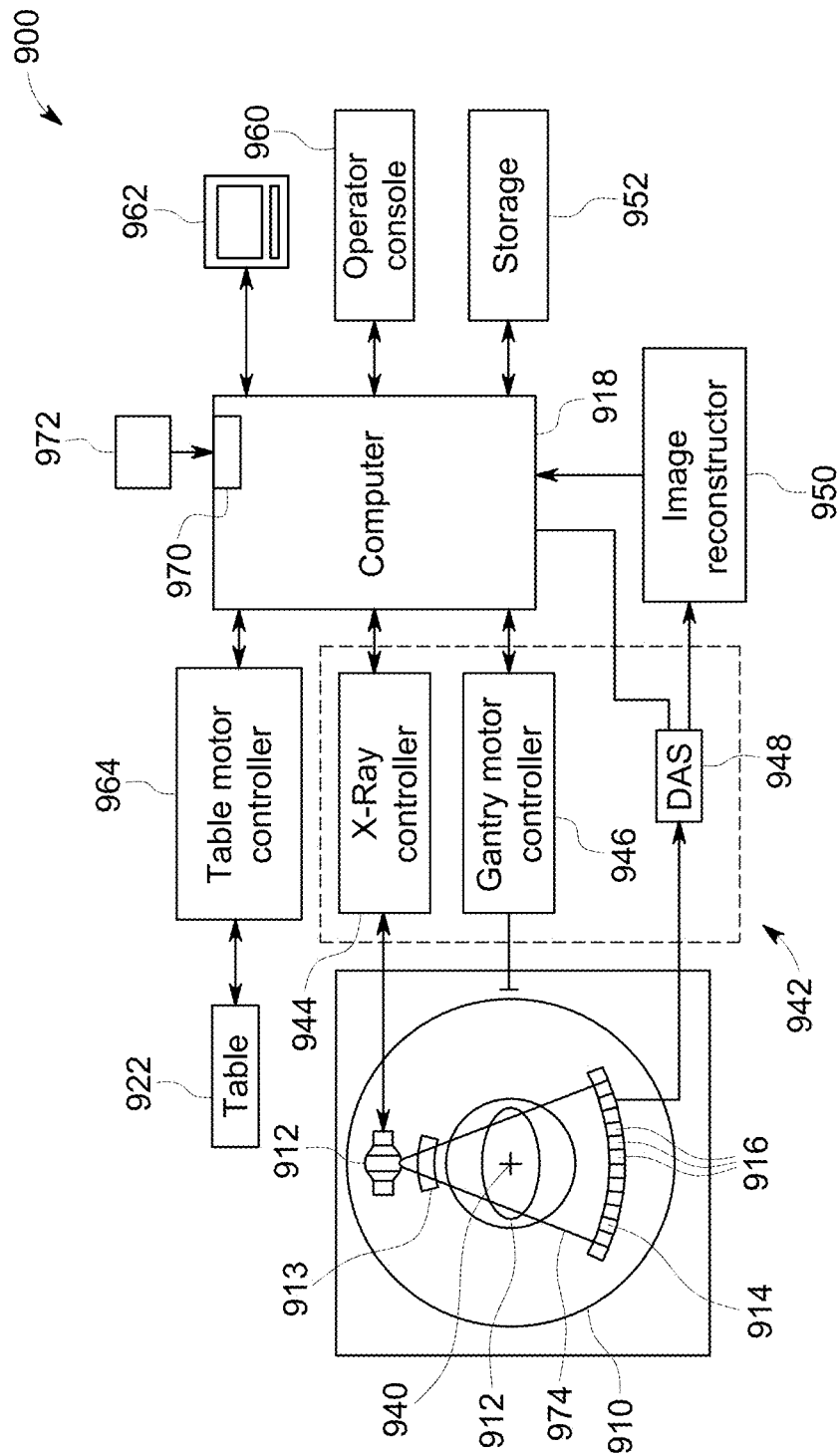
FIG. 12 is a schematic block diagram of an imaging system in accordance with various embodiments.

Various methods and/or systems (and/or aspects thereof) described herein may be implemented using a medical imaging system. For example, FIG. 12 is a block schematic diagram of an exemplary CT imaging system 900 that may be utilized to implement various embodiments discussed herein. Although the CT imaging system 900 is illustrated as a standalone imaging system, it should be noted that the CT imaging system 900 may form part of a multi-modality imaging system in some embodiments. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays 974 toward the detector array 914 on the opposite side of the gantry 910. A source collimator 913 and a bowtie filter module (not shown in FIG. 12) are provided proximate the X-ray source 912. In various embodiments, the source collimator 913 may be configured to provide wide collimation as discussed herein. The detector array 914 includes a plurality of detector elements 916 that are arranged in rows and channels that together sense the projected X-rays that pass through a subject 917. The CT imaging system 900 also includes a computer 918 that receives the projection data from the detector array 914 and processes the projection data to reconstruct an image of the subject 917. The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject 917 into and out of the gantry 910. Particularly, the motorized table 922 moves at least a portion of the subject 917 through a gantry opening (not shown) that extends through the gantry 910. Further, the motorized table 922 may be used to move the subject 917 vertically within the bore of the gantry 910.

The depicted detector array 914 includes a plurality of detector elements 916. Each detector element 916 produces an electrical signal, or output, that represents the intensity of an impinging X-ray beam 974 and hence allows estimation of the attenuation of the beam as it passes through the subject 917. During a scan to acquire the X-ray projection data, the gantry 910 and the components mounted thereon rotate about a center of rotation 940. FIG. 12 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer 918. It may be noted that one or more of the computer 918, controllers, or the like may be incorporated as part of a processing unit such as the processing unit 120 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the motorized table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view" or "projection." A "scan" of the subject 917 comprises a set of views made at different gantry angles, or view angles, during one or more revolutions of the X-ray source 912 and the detector array 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35

U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An imaging system comprising:
   a computed tomography (CT) acquisition unit comprising an X-ray source and a CT detector configured to collect CT imaging data of an object to be imaged, the X-ray source and the CT detector configured to be rotated about the object to be imaged and to collect a series of projections of the object as the X-ray source and the CT detector rotate about the object to be imaged; and
   a processing unit comprising at least one processor operably coupled to the CT acquisition unit, the processing unit configured to:
      control the CT acquisition unit to collect, at a reference view angle, a reference projection;
      control the CT acquisition unit to collect at least one sample projection during rotation of the CT acquisition unit about the object to be imaged,
      compare an intensity of the at least one sample projection to an intensity of the reference projection, wherein the intensity of the at least one sample projection and the intensity of the reference projection are measured intensities,
      select a time to perform an imaging scan based on the comparison of the intensity of the at least one sample projection to the intensity of the reference projection, and
      control the CT acquisition unit to perform the imaging scan.

2. The imaging system of claim 1, wherein the processing unit is further configured to remove information corresponding to high density structures from the reference projection and the at least one sample projection before comparing the intensity of the at least one sample projection and the reference projection.

3. The imaging system of claim 1, wherein the processing unit is configured to collect plural candidate projections during each rotation of the CT acquisition unit and to select the at least one sample projection from the plural candidate projections based on a similarity of an angle at which the at least one sample projection was obtained to the reference view angle at which the reference projection was obtained.

4. The imaging system of claim 1, wherein the processing unit is configured to control the CT acquisition unit to perform the imaging scan at a time corresponding to an arterial phase of a perfusion study, wherein the time is selected to correspond to a threshold corresponding to a maximum intensity, and to perform an additional imaging scan at a time corresponding to a venous phase of a perfusion study, wherein the time to perform the additional imaging scan is selected to correspond to a threshold corresponding to a minimum intensity.

5. The imaging system of claim 1, wherein the processing unit is configured to control the CT acquisition unit to collect plural sample projections at different times and to determine a cardiac output based on intensities of the plural sample projections preceding an arterial phase of a perfusion study.

6. The imaging system of claim 1, further comprising a collimator configured to be interposed between the X-ray source and the object to be imaged, the collimator configured to provide wide collimation, wherein the at least one sample projection is taken along a longitudinal view of the object.

7. The imaging system of claim 6, wherein the processing unit is configured to control the CT acquisition unit to collect plural sample projections at different times and to determine a contrast flow rate using the plural sample projections acquired at different times.

8. The imaging system of claim 7, wherein the processing unit is further configured to adjust at least one of pitch, rotation time, or table speed based on the contrast flow rate determined using the plural sample projections.

9. The imaging system of claim 1, wherein the processing unit is further configured to obtain the reference projection and the at least one sample projection with the reference projection and at least one sample projection not including enough information to provide a diagnostically useful image.

10. A method comprising:
    obtaining, with a CT acquisition unit, a reference projection at a reference view angle;
    obtaining, with the CT acquisition unit, at least one sample projection of CT imaging information during rotation of the CT acquisition unit about an object to be imaged;
    comparing an intensity of the at least one sample projection to an intensity of the reference projection, wherein the intensity of the at least one sample projection and the intensity of the reference projection are measured intensities;
    selecting a time to perform an imaging scan based on the comparing of the intensity of the at least one sample projection to the intensity of the reference projection; and
    controlling the CT acquisition unit to perform the imaging scan based on the selected time.

11. The method of claim 10, wherein obtaining at least one sample projection of CT imaging information during rotation of the CT acquisition unit about an object to be imaged further comprising:
    collecting plural candidate projections during a rotation of the CT acquisition unit; and
    selecting the at least one sample projection from the plural candidate projections based on a similarity of an angle at which the at least one sample projection was obtained to the reference view angle at which the reference projection was obtained.

12. The method of claim 10, wherein the object is a human patient, wherein controlling the CT acquisition unit to perform the imaging scan based on the selected time comprises performing the imaging scan on a head of the human patient, and wherein obtaining at least one sample projection of CT imaging information during rotation of the CT acquisition unit comprises obtaining the at least one sample projection from a view oriented laterally of the human patient.

13. The method of claim 10, wherein the object is a human patient, wherein controlling the CT acquisition unit to perform the imaging scan based on the selected time comprises performing the imaging scan on a torso of the human patient and wherein obtaining at least one sample projection of CT imaging information during rotation of the CT acquisition unit comprises obtaining the at least one sample projection from a view oriented at least one of anteriorly or posteriorly of the human patient.

14. The method of claim 10, wherein obtaining at least one sample projection of CT imaging information during rotation if the CT acquisition unit about an object to be imaged comprises: obtaining plural sample projections, and determining corresponding intensities of the plural sample projections, and determining a cardiac output based on the corresponding intensities.

15. The method of claim 10, wherein obtaining at least one sample projection of CT imaging information during rotation of the CT acquisition unit about an object to be imaged comprises obtaining the at least one sample projection along a longitudinal view of the object.

16. The method of claim 15, wherein obtaining at least one sample projection of CT imaging information during rotation of the CT acquisition unit about an object to be imaged comprises obtaining plural sample projections at different times, further comprising determining a contrast flow rate using the plural sample projections acquired at different times.

17. The method of claim 16, further comprising adjusting at least one of pitch, rotation time, or table speed based on the contrast flow rate determined using the plural sample projections.

18. A tangible and non-transitory computer readable medium comprising one or more computer software modules configured to direct one or more processors to:
obtain, via a computed tomography (CT) acquisition unit, a reference projection at a reference view angle;
obtain, via the CT acquisition unit, at least one sample projection of CT imaging information during rotation of the CT acquisition unit about an object to be imaged;
compare an intensity of the at least one sample projection to an intensity of the reference projection, wherein the intensity of the at least one sample projection and the intensity of the reference projection are measured intensities;
select a time to perform an imaging scan based on the comparison of the intensity of the at least one sample projection to the intensity of the reference projection; and
control the CT acquisition unit to perform the imaging scan based on the selected time.

19. The tangible and non-transitory computer readable medium of claim 18, wherein the computer readable medium is further configured to direct the one or more processors to collect plural candidate projections during a rotation of the CT acquisition unit and select the at least one sample projection from the plural candidate projections based on a similarity of an angle at which the at least one sample projection was obtained to the reference view angle at which the reference projection was obtained.

20. The tangible and non-transitory computer readable medium of claim 18, wherein the computer readable medium is further configured to obtain plural sample projections and determine corresponding intensities of the plural sample projections, and determine a cardiac output based on the corresponding intensities.

21. The tangible and non-transitory computer readable medium of claim 18, wherein the computer readable medium is further configured to direct the one or more processors to obtain plural sample projections at different times, wherein the at least one sample projection is taken along a longitudinal view of the object, and wherein the computer readable medium is further configured to determine a contrast flow rate using the plural sample projections acquired at different times.

* * * * *